US012805739B2

(12) United States Patent
El Katerji et al.

(10) Patent No.: US 12,805,739 B2
(45) Date of Patent: Nov. 24, 2026

(54) SYSTEMS AND METHODS FOR DETERMINING CARDIAC PERFORMANCE

(71) Applicants: ABIOMED, Inc., Danvers, MA (US); Massachusetts Institute of Technology, Cambridge, MA (US); The Brigham and Women's Hospital Inc., Boston, MA (US)

(72) Inventors: Ahmad El Katerji, Danvers, MA (US); Qing Tan, Danvers, MA (US); Christian Moyer, Danvers, MA (US); Alexander Ship, Danvers, MA (US); Sonya Sanat Bhavsar, Danvers, MA (US); Noam Josephy, Danvers, MA (US); Elazer R. Edelman, Cambridge, MA (US); Brian Yale Chang, Cambridge, MA (US); Steven Keller, Cambridge, MA (US)

(73) Assignees: Abiomed, Inc., Danvers, MA (US); Massachusetts Institute of Technology, Cambridge, MA (US); The Brigham and Women's Hospital Inc., Boston, MA (US)

( * ) Notice: Subject to any disclaimer, the term of this patent is extended or adjusted under 35 U.S.C. 154(b) by 157 days.

(21) Appl. No.: 18/939,182

(22) Filed: Nov. 6, 2024

(65) Prior Publication Data

US 2025/0210205 A1 Jun. 26, 2025

Related U.S. Application Data

(62) Division of application No. 17/734,819, filed on May 2, 2022, now Pat. No. 12,179,009, which is a division
(Continued)

(51) Int. Cl.
*A61B 5/029* (2006.01)
*A61B 5/021* (2006.01)
(Continued)

(52) U.S. Cl.
CPC .......... *A61B 5/029* (2013.01); *A61B 5/02141* (2013.01); *A61B 5/0215* (2013.01);
(Continued)

(58) Field of Classification Search
None
See application file for complete search history.

(56) References Cited

U.S. PATENT DOCUMENTS 3,677,092 A 7/1972 Guarino
4,598,579 A 7/1986 Cummings et al.
(Continued)

FOREIGN PATENT DOCUMENTS

CN 103315730 A 9/2013
CN 104244814 A 12/2014
(Continued)

OTHER PUBLICATIONS

Office Action from corresponding Canadian Patent Application No. 3,103,478 dated Mar. 16, 2026 (4 pp).
(Continued)

*Primary Examiner* — Kennedy Schaetzle
(74) *Attorney, Agent, or Firm* — Botos Churchill IP Law LLP

(57) ABSTRACT

The systems and methods described herein determine metrics of cardiac performance via a mechanical circulatory support device and use the cardiac performance to calibrate, control and deliver mechanical circulatory support for the heart. The systems include a controller configured to operate the device, receive inputs indicative of device operating conditions and hemodynamic parameters, and determine
(Continued)

vascular performance, including vascular resistance and compliance, and native cardiac output. The systems and methods operate by using the mechanical circulatory support device (e.g., a heart pump) to introduce controlled perturbations of the vascular system and, in response, determine heart parameters such as stroke volume, vascular resistance and compliance, left ventricular end diastolic pressure, and ultimately determine native cardiac output.

8 Claims, 9 Drawing Sheets

Related U.S. Application Data of application No. 16/446,419, filed on Jun. 19, 2019, now Pat. No. 11,357,968.

(60) Provisional application No. 62/863,146, filed on Jun. 18, 2019, provisional application No. 62/863,136, filed on Jun. 18, 2019, provisional application No. 62/687,133, filed on Jun. 19, 2018.

(51) Int. Cl.
*A61B 5/0215* (2006.01)
*A61M 60/216* (2021.01)
*A61M 60/50* (2021.01)
*A61M 60/515* (2021.01)
*A61M 60/523* (2021.01)
*A61M 60/531* (2021.01)
*A61M 60/538* (2021.01)
*A61M 60/135* (2021.01)
*A61M 60/411* (2021.01)

(52) U.S. Cl.
CPC .......... *A61M 60/216* (2021.01); *A61M 60/50* (2021.01); *A61M 60/515* (2021.01); *A61M 60/523* (2021.01); *A61M 60/531* (2021.01); *A61M 60/538* (2021.01); *A61M 60/135* (2021.01); *A61M 60/411* (2021.01); *A61M 2205/3334* (2013.01); *A61M 2205/3344* (2013.01); *A61M 2230/04* (2013.01)

(56) References Cited

U.S. PATENT DOCUMENTS 4,877,035 A 10/1989 Bogen et al.
5,241,966 A 9/1993 Finkelstein et al.
5,365,933 A 11/1994 Elghazzawi
5,400,793 A * 3/1995 Wesseling .............. A61B 5/029 600/526
5,437,284 A 8/1995 Trimble
5,535,753 A 7/1996 Petrucelli et al.
5,964,694 A 10/1999 Siess et al.
6,116,862 A 9/2000 Rau et al.
6,159,160 A 12/2000 Hsei et al.
6,176,822 B1 1/2001 Nix et al.
6,234,759 B1 5/2001 Hennel et al.
6,485,431 B1 11/2002 Campbell
6,623,420 B2 9/2003 Reich et al.
6,949,066 B2 9/2005 Bearnson et al.
7,010,954 B2 3/2006 Siess et al.
7,022,100 B1 4/2006 Aboul-Hosn et al.
8,282,564 B2 10/2012 Parlikar et al.
8,282,664 B2 10/2012 Nance et al.
10,426,878 B2 10/2019 Franano
11,246,497 B2 2/2022 Jansen et al.
2003/0139643 A1 7/2003 Smith et al.
2004/0039243 A1 2/2004 Bearnson et al.
2004/0106874 A1 6/2004 Eigler et al.
2004/0254483 A1 12/2004 Zdeblick et al.
2005/0187481 A1 8/2005 Hatib et al.
2006/0235323 A1 10/2006 Hatib et al.
2008/0097226 A1 4/2008 McConnell
2008/0183232 A1 7/2008 Voss et al.
2009/0270739 A1 10/2009 Hatib et al.
2010/0056931 A1 3/2010 Soffer et al.
2010/0076326 A1 3/2010 Cohen et al.
2010/0125211 A1 5/2010 Stahmann et al.
2010/0204590 A1 8/2010 Hatib et al.
2010/0217134 A1 8/2010 Van Goudoever et al.
2010/0268333 A1 10/2010 Gohean et al.
2013/0041204 A1 2/2013 Heilman et al.
2013/0046129 A1 2/2013 Medvedev et al.
2013/0253359 A1 9/2013 Emtell et al.
2013/0338559 A1 12/2013 Franano et al.
2014/0107505 A1 4/2014 Marmor et al.
2014/0243696 A1 8/2014 Peyton
2014/0296615 A1 10/2014 Franano
2015/0018632 A1 1/2015 Khair
2015/0246166 A1 9/2015 Greatrex et al.
2016/0367740 A1 12/2016 Aboul-Hosn et al.
2017/0065186 A1 3/2017 Joseph et al.
2017/0136164 A1 5/2017 Yeatts
2017/0239407 A1 8/2017 Hayward
2018/0078159 A1 3/2018 Edelman et al.
2018/0146864 A1 5/2018 Jansen et al.
2019/0351118 A1* 11/2019 Graichen ............ A61M 60/816
2021/0052791 A1 2/2021 Granegger

FOREIGN PATENT DOCUMENTS

CN 107847649 A 3/2018
EP 1348373 A1 10/2003
EP 1358840 A2 11/2003
EP 3197517 A2 8/2017
JP 2006528006 A 12/2006
JP 2008279048 A 11/2008
JP 2012501218 A 1/2012
JP 2014528771 A 10/2014
JP 2017522147 A 8/2017
JP 2019532700 A 11/2019
KR 20020002493 A 1/2002
KR 20030071640 A 9/2003
KR 20030082368 A 10/2003
KR 101630124 B1 6/2016
WO 9749439 A1 12/1997
WO 9843688 A1 10/1998
WO 0064339 A1 11/2000
WO 2004017818 A2 3/2004
WO 2005006975 A1 1/2005
WO 2013171599 A1 11/2013
WO 2014062911 A2 4/2014
WO 2016044889 A2 3/2016
WO 2016195477 A1 12/2016
WO 2017102164 A1 6/2017
WO 2018036927 A1 3/2018
WO 2018053504 A1 3/2018
WO 2018073150 A1 4/2018
WO 2018146045 A1 8/2018

OTHER PUBLICATIONS

Office Action from corresponding New Zealand Patent Application No. 771871 dated Oct. 24, 2024 (7 pp.).
Written Opinion for Singapore Patent Application No. 11202012262X dated Feb. 27, 2025 (6 pp.).
Office Action issued in Japanese Patent Application No. 2024-088136 on Aug. 20, 2025 (5 pp).
Office Action issued in Indian Patent Application No. 202117001343, dated Jan. 29, 2026, 25 pp.
Daniel Ruschen et al: “Online cardiac output estimation during transvalvular left ventricular assistance”, Computer Methods and Programs in Biomedicine vol. 171, Aug. 30, 2016 (Aug. 30, 2016), pp. 87-97.
Daniel Ruschen et al: Robust Assistance Control of Left Ventric. Assist Dev. 11, EMBEC & NBC 2017. EMBEC 2017, NBC 2017. IFMBE PRO., vol. 65. Springer, Singapore, vol. 65, (Jun. 13, 2017),

(56) References Cited

OTHER PUBLICATIONS

XP055614768, DOI: https://doi.org/10.1007/978-981-10-5122-7-74.
Examination Report issued in Indian Patent Application No. 202117001343 mailed Oct. 13, 2022, 8 pages.
Extended European Search Report from European Patent Application No. 23178946.2 dated Aug. 25, 2023 (10 pp.).
International Search Report and Written Opinion for Application No. PCT/US2019/038039 dated Sep. 5, 2019.
International Search Report for Application No. PCT/US2018/036757 dated Sep. 10, 2018 (5 pages).
International Search Report for Application No. PCT/US2019/038049 dated Sep. 5, 2019 (6 pages).
International Search Report PCT/US2017/052259 dated Dec. 19, 2017 (3 pages).
Notification to Grant Patent Right for Invention in Chinese Application No. 201980054311.7, issued Oct. 15, 2024.
Office Action dated Dec. 12, 2023 for Israeli Appln. No. 279524 (4 pp.).
Office Action dated Jul. 9, 2024 in Japanese Application No. 2024-088136 (4 pp.).
Office Action from Australian Patent Application No. 2019290139, dated Mar. 13, 2024 (4 pp.).
Office Action from Australian Patent Application No. 2019290143 dated Apr. 17, 2024 (4 pp.).
Office Action from Chinese Patent Application No. 201980054311.7 dated Sep. 27, 2023 (23 pp.).
Office Action from Chinese Patent Application No. 201980054368.7 dated Sep. 22, 2023 (18 pp.).
Office Action from Indian Application No. 202117001344 dated Sep. 22, 2022 (7 pages).
Office Action from Israeli Patent Application No. 279432 dated Oct. 22, 2023 (4 pp.).
Office Action from Israeli Patent Application No. 279524 dated Dec. 11, 2023 (4 pp.).
Office Action from Japanese Patent Application No. 2020-570922 dated Jan. 26, 2024 (6 pp.).
Office Action from Japanese Patent Application No. 2020-570922 dated Jul. 19, 2023 (8 pp.).
Office Action from Japanese Patent Application No. 2020-570922 dated Mar. 2, 2023 (5 pp.).
Office Action from Japanese Patent Application No. 2021-520094 dated Aug. 16, 2023 (6 pp.).
Office Action from Japanese Patent Application No. 2021-520094 dated Feb. 20, 2023 (11 pp.).
Office Action from Japanese Patent Application No. 2021-520094 dated May 30, 2024 (4 pp.).
Office Action from Korean Patent Application No. 10-2021-7001285 dated Apr. 8, 2024 (16 pp.).
Office Action from New Zealand Patent Application No. 771868 dated Aug. 28, 2024 (3 pp.).
Office Action issued in Korean Patent Application No. 10-2021-7001258, mailed Apr. 8, 2024, 18 pages.
Office Action with Search Report dated Jun. 19, 2024 for Chinese Application No. 201980054368.7, (20 pp.).
Rüschen, D., Online cardiac output estimation during transvalvular left ventricular assistance, Computer Methods and Programs in Biomedicine, http://dx.doi.org/doi:10.1016/j.cmpb.2016.08.020 (24 pp.).
Search Report and Written Opinion from Singapore Application No. 11202012264T dated Aug. 12, 2022 (10 pages).
Search Report issued in Singapore Patent Application No. 11202012262X dated Jul. 26, 2022, 3 pages.
Sekii H et al: "Beat-to-beat prediction of left ventricular output during left ventricular bypass pumping", Pro. of the Ann. Inter. Conf. of the IEEE Eng. in Med. and Bio. Soc. Paris, FR., Oct. 29-Nov. 1, 1992, IEEE, NY, NY, USA, (Nov. 4, 1988), p. 1773.
Stolinski, et al., "The heart-pump interaction: Effects of a microaxial blood pump", International Journal of Artificial Organs, vol. 25, No. 11, pp. 1082-1088 (2002).
Written Opinion issued in Singapore Patent Application No. 11202012262X dated Aug. 19, 2022, 7 pages.
Ruschen, Daniel, et al., "Online cardiac output estimation during transvalvular left ventricular assistance", Computer Methods and Programs in Biomedicine 171 (2019), 2019, pp. 87-97.
Hearing Notice for Indian Patent Application No. 202117001343, Aug. 5, 2025, 4 Pages.
Office Action from corresponding Canadian Patent Application No. 3,102,885 dated Mar. 19, 2026 (7 pp).
Office Action issued in Australian Patent Application No. 2025204555 on Jun. 11, 2026 (3 pp.).

* cited by examiner

SYSTEMS AND METHODS FOR DETERMINING CARDIAC PERFORMANCE

CROSS-REFERENCE TO RELATED APPLICATIONS

The present application is a divisional of U.S. patent application Ser. No. 17/734,819, filed May 2, 2022, now U.S. Pat. No. 12,179,009allowed, which is a divisional of U.S. patent application Ser. No. 16/446,419, filed Jun. 19, 2019, now U.S. Pat. No. 11,357,968, which claims the benefit of U.S. Provisional Patent Application No. 62/687,133, filed Jun. 19, 2018, U.S. Provisional Patent Application No. 62/863,136, filed Jun. 18, 2019, and U.S. Provisional Patent Application No. 62/863,146, filed Jun. 18, 2019, the disclosures of all of which are hereby incorporated by reference in their entirety.

BACKGROUND OF THE INVENTION

Cardiovascular diseases are a leading cause of morbidity, mortality, and burden on global healthcare. A variety of treatment modalities have been developed for heart health, ranging from pharmaceuticals to mechanical devices and transplantation. Temporary cardiac support devices, such as heart pump systems, provide hemodynamic support and facilitate heart recovery. Some heart pump systems are percutaneously inserted into the heart and can run in parallel with the native heart to supplement cardiac output. Examples of such devices include the IMPELLA® family of devices (Abiomed, Inc., Danvers MA). Such heart pump systems have sensors that detect blood pressure (or assess differential pressures across membranes) and can monitor motor current, and use the sensor and motor current readings to help identify pump positioning.

The cardiac support needed by a given patient can vary from patient to patient. Cardiac output (CO) is the volumetric flow of blood delivered by the heart. Normal cardiac output is about 5 L/min in a healthy adult but can vary based on various factors including physical make up of a given patient. It is difficult for clinicians to quantitatively determine, using known techniques, how much cardiac output a given heart provides, how much additional support a device should deliver, when to deliver it, and for how long. The determination can be particularly challenging for patients who are recovering from intervention or other cardiac care. Thus, clinicians tend to rely on judgments and indirect estimates of cardiac function, such as measuring intracardiac or intravascular pressures using fluid filled catheters. Cardiac output (CO) in particular is difficult to quantify. One technique uses pulmonary artery catheters (PAC) to provide real-time measures of central venous pressure and pulmonary artery pressure. PAC's rely on estimates of CO using Fick's laws through measures of systemic oxygen consumption or bolus thermodilution methods. But because of the assumptions that must be made to arrive at CO metrics and the corresponding lack of precision, PACs can be of limited use in high risk situations, such as complex intervention and cardiogenic shock. Measurements through PACs discount dynamic changes in cardiac function and are not continuous, while non-linear aspects of systemic ventricular vascular coupling may not be addressed.

BRIEF SUMMARY OF THE INVENTION

The systems and methods described herein determine metrics of vascular and/or cardiac performance, such as CO, via a mechanical circulatory support device, for example an intravascular blood pump system, and use the cardiac performance to calibrate, control and deliver mechanical circulatory support for the heart. The systems include a mechanical circulatory support device and a controller configured to operate the device, receive inputs indicative of device operating conditions and hemodynamic parameters, and determine vascular performance, including vascular resistance and compliance, and native cardiac output. The systems and methods operate by using the mechanical circulatory support device (e.g., a heart pump) to introduce controlled perturbations of the vascular system and, in response, determine heart parameters such as stroke volume, vascular resistance and compliance, cardiac contractility, ventricular elastance, CO and left ventricular end diastolic pressure, and ultimately determine native cardiac output. Those determined parameters can then be used for calibrating and controlling further mechanical circulatory support for the heart. By determining the native cardiac output of the heart, a therapeutic regimen can be applied using mechanical circulatory support (e.g., a blood pump). To effect the therapy, the process control system actuates or deactuates the mechanical circulatory support device (e.g., the pump) for delivering and adjusting the level of support.

The systems and methods are configured with a time-variant non-linear model of the vascular system and use device-arterial coupling to continuously determine systemic vascular resistance and compliance, and thereby quantify cardiac stroke volume. In some implementations the systems and methods use a Windkessel model of the vascular system to improve traditional linear approximations and provide for dynamic variation of the vascular response. In some embodiments, the systems and methods are configured as a cardiac output sensor that can directly determine the native cardiac output of a patient's heart.

In various adaptations, the systems and methods are configured to "ping" the vasculature during a heartbeat using a mechanical circulatory support system and then detect the response by the heart at one or more later periods or points in time, for example during a later heartbeat. "Pinging" involves increasing or decreasing the output of the mechanical circulatory support system (e.g., increasing or decreasing the pump speed of a heart pump system) for a brief time period, for example within a single heartbeat, thereby generating a spike in blood pressure and flow (e.g., aortic pressure and blood flow leaving the left ventricle). The ping alters a hemodynamic parameter (e.g., the aortic pressure) from its baseline, and that alteration is detected and compared to the hemodynamic parameter at another time (e.g., the aortic pressure when the heart is not being pinged) to determine cardiac performance. Pinging may entail altering pump speed during a time period (or at a point in time) within a portion of a single heartbeat (e.g., during a phase of a heartbeat) and comparing a hemodynamic parameter during this "altered" time to a hemodynamic parameter during a "normal" operation period or point in time (e.g., during a subsequent heartbeat) when the ping is not applied.

Example hemodynamic parameters include heart rate, blood pressure, arterial oxygen saturation, mixed venous saturation, central venous oxygen saturation, arterial blood pressure, mean arterial pressure, right arterial pressure, central venous pressure, right ventricular pressure, pulmonary artery pressure, mean pulmonary artery pressure, pulmonary artery occlusion pressure, left atrial pressure, aortic pressure, differential pressure, left ventricular end pressure, stroke volume, stroke volume index, stroke volume variation, systemic vascular resistance, systemic vascular resistance index, pulmonary vascular resistance, pulmonary vascular resistance index, pulmonary vascular resistance, pulmonary vascular resistance index, left ventricular stroke work, left ventricular stoke work index, right ventricular stroke work, right ventricular stroke work index, coronary artery perfusion pressure, right ventricular end diastolic volume, right ventricular end diastolic volume index, right ventricular end systolic volume, right ventricular ejection fraction, arterial oxygen content, venous oxygen content, arterial-venous oxygen content difference, oxygen delivery, oxygen delivery index, oxygen consumption, oxygen consumption index, oxygen extraction ration, oxygen extraction index, total peripheral resistance, CO, cardiac index, and cardiac power output (CPO).

Intrabeat pinging (i.e., adjusting pump operation within a single heartbeat) allows comparison of hemodynamic parameters that occur between heartbeats (either sequentially adjacent to each other, or spaced apart by other beats), while also minimizing noise (e.g., sympathetic responses) that may arise if the pump speed is altered for a longer period of time. As mentioned above, in some embodiments, hemodynamic parameter comparison is accomplished by a control system processor that is programmed with a model of the vascular system, such as a two-element Windkessel model, that models and accounts for changing, non-linear interactions between pump flow and heart operation. The control system uses known terms (received as inputs) to approximate the values for pump flow and heart operation (e.g., aortic pressure), which allows such models to be readily validated and utilized in clinical applications. The systems and methods provide metrics indicative of patient heart health, such as resistance and compliance of the systemic vasculature, which allows for the determination of CO and other aspects of cardiac performance. In some applications, the systems and methods are deployed without the need for additional measurements or diagnostic catheters. The potential to continuously and accurately track changes in systemic vascular performance (e.g., resistance and compliance) and estimate cardiac stroke volume marks a significant advancement over traditional measures obtained from a PAC or other diagnostics deployed in current clinical practice.

In some adaptations, the systems and methods described herein alter pump speed of a heart pump system within a single heartbeat to detect its impact on the vascular performance. That can be done by comparing the changes in one or more hemodynamic parameters during a "normal" or "reference" heartbeat (e.g., a heartbeat when the heart pump system is operating at a first pump speed) and during a "modulated" heartbeat (e.g., a heartbeat when the heart pump system is operating at a different pump speed than the first pump speed for at least a portion of the heartbeat). The reference heartbeat may occur before or after the modulated heartbeat. By modulating or "pinging" a heartbeat, the systems and methods can capture and quantify the differences in the hemodynamic parameter between the normal heartbeat and the modulated heartbeat. These differences are then correlated with differences in flow, stroke volume, CO, or other useful metrics of vascular and/or cardiac performance. By changing the pump speed for a short period of time (e.g., a fraction of a heartbeat), systemic resistance and compliance can be quantified at a variety of pump speeds with more real time accuracy and without introducing additional noise to the system measurements.

In some implementations, a controller is provided and configured to perform any of the implementations, aspects, and methods described herein. For example, the controller may be the Automated Impella Controller (AIC) of Abiomed, Inc or any other suitable controller programmed to carry out the disclosed functionality. In some implementations, the systems and methods use a mechanical circulatory support device, such as a heart pump. Example heart pumps include a catheter; a motor; a rotor operatively coupled to the motor; a pump housing at least partially surrounding the rotor so that the actuating motor drives the rotor and pumps blood through the pump housing; one or more sensors, such as a differential pressure sensor; and the controller. For example, the heart pump system may comprise a blood pump with a cannula configured to be deployed within the heart, and a motor positioned either within or outside the heart and configured to drive the pump. The heart pump system may be the Impella 3.5 heart pump of Abiomed, Inc connected to an AIC or any other suitable control system.

The systems and methods described herein alter the operation of a mechanical circulatory device within a heartbeat in order to compare one or more monitored hemodynamic parameters during that phase with the same parameters during a different beat and thus compute a metric indicative of vascular performance of the patient. For example, a pump may be inserted intravascularly and operated at a first pump speed (or other output level) during a baseline series of heartbeats including a first heartbeat, and then the heart is "pinged" by increasing or decreasing the pump speed for a very short period of time during a second, or target heartbeat, or during a particular phase of the target heartbeat (e.g., at or after the dicrotic notch during the target heartbeat). The aortic pressure or other hemodynamic parameter is measured during both the baseline series and during the target heartbeat. In some adaptations, the hemodynamic parameter is measured during the same part of the first heartbeat and the second heartbeat (e.g., during systole in both beats, or at or after the dicrotic notch in both beats). The system then compares the hemodynamic parameter, for example aortic pressure, identified during the baseline series (e.g., during the first heartbeat) to that hemodynamic parameter identified during the time of increased pump speed (e.g., during the second heartbeat) for example by using the same sensor and calculates or characterizes vascular resistance or compliance, which may be used to determine CO or alter operation of the pump to better treat the patient. The baseline series of heartbeats (e.g., including the first heartbeat) may occur after the ping, or before it. Such methods may be performed using the heart pump system 100 of FIG. 1 described below or any other suitable pump.

To implement the systems and methods, a pump or other mechanical circulatory support device is positioned within the patient's vasculature (e.g., in the patient's heart) and operable to alter the patient's hemodynamics. For example, the device's operation may increase the patient's aortic pressure by unloading the left ventricle or other means. In some implementations, the pump is an intravascular blood pump device placed within the patient's heart via percutaneous insertion. The pump may also be a surgically implanted device, a left ventricular assist device, a counterpulsation device, an expandable heart pump, an extracorporeal membrane device, or any other suitable device. The pump may be appropriate because the patient is in cardiogenic shock or otherwise experiencing a decline in vascular health. The pump may be positioned across the aortic valve such that a blood inlet to the pump is within the left ventricle and an outlet from the pump is within the aorta. The pump contributes to native heart operation such that:

$$CO = i_h + i_p \quad (1)$$

where CO is total cardiac output, $i_h$ is native cardiac output, and $i_p$ is flow contributed by the pump. Such pumps may provide lifesaving advantages for patients in cardiogenic shock by increasing oxygenated blood flow from the heart and into the coronary and other areas of the vasculature.

Hemodynamic parameters are monitored while operating the pump or other mechanical circulatory support system (for example, the parameter may be monitored continuously during cardiac performance and relevant data indicative of the parameter at selected times during selected beats may be identified for use). Suitable hemodynamic parameters include parameters relating to the flow of blood within the organs and tissues of the body. Example hemodynamic parameters include heart rate, blood pressure, arterial oxygen saturation, mixed venous saturation, central venous oxygen saturation, arterial blood pressure, mean arterial pressure, right arterial pressure, central venous pressure, right ventricular pressure, pulmonary artery pressure, mean pulmonary artery pressure, pulmonary artery occlusion pressure, left atrial pressure, aortic pressure, differential pressure, left ventricular end pressure, stroke volume, stroke volume index, stroke volume variation, systemic vascular resistance, systemic vascular resistance index, pulmonary vascular resistance, pulmonary vascular resistance index, pulmonary vascular resistance, pulmonary vascular resistance index, left ventricular stroke work, left ventricular stoke work index, right ventricular stroke work, right ventricular stroke work index, coronary artery perfusion pressure, right ventricular end diastolic volume, right ventricular end diastolic volume index, right ventricular end systolic volume, right ventricular ejection fraction, arterial oxygen content, venous oxygen content, arterial-venous oxygen content difference, oxygen delivery, oxygen delivery index, oxygen consumption, oxygen consumption index, oxygen extraction ration, oxygen extraction index, total peripheral resistance, CO, cardiac index, and cardiac power output (CPO). In some implementations, differential pressure ($P_{diff}$) may be used in place of aortic pressure for calculations during diastole (for example, if differential pressure is known and aortic pressure is not). $P_{diff}$ is equal to the aortic pressure minus the left ventricular pressure (LVP). In many instances, LVP is much smaller than aortic pressure during diastole and, compared to aortic pressure, does not vary much during the diastolic period. For these cases, $P_{diff}$ is close enough to aortic pressure (i.e., LVP is negligible) that it can serve as a surrogate if AoP is not available. The accuracy of results in certain calculations described herein may be affected if $P_{diff}$ is used in place of aortic pressure.

The pump speed is the speed of operation of the pump and corresponds to the amount of blood flow provided by the pump's operation. In some implementations, the pump speed corresponds to a speed of rotation of a rotor. For example, the pump speed may be 10,000 RPM, 20,000 RPM, 30,000 RPM, 40,000 RPM, 50,000 RPM, 60,000 RPM, 70,000 RPM, 80,000 RPM, 90,000 RPM, 100,000 RPM, or any suitable speed. A pump speed may correspond to a power level, or P-level, as described above in relation to FIG. 1. For example, the pump speed is P-1, P-2, P-3, P-4, P-5, P-6, P-7, P-8, P-9, or any other suitable value. In some implementations, the pump speed instead corresponds to the rate at which a chamber of the pump fills and releases blood. By monitoring a hemodynamic parameter, the systems and methods described herein may detect changes in that hemodynamic parameter over time. Such changes may be used to quantify heart performance.

In some implementations, a heartbeat detection method is provided by measuring a hemodynamic parameter during heart performance (e.g., during multiple heartbeats), identifying and predicting various heart phases and their alignment in time, and then determining when to adjust pump speed or otherwise ping the heart, based on a prediction of when a subsequent heart phase will occur. A first (baseline) phase of a heartbeat in a heartbeat cycle may be identified as the heart's systolic period, its diastolic period, or any other suitable phase or combination of phases, which takes place over a first period of time during heart performance. For example, the first period of time may be 0.05 seconds, 0.1 seconds, 0.2 seconds, 0.3 seconds, or any suitable length of time for the given heartbeat or other cycle.

In a second step, a second phase of the heartbeat cycle is predicted or otherwise identified to serve as the target phase when the heart should receive the "ping." For example, the second phase may be a second heartbeat, a different systolic period, a different diastolic period, or any other suitable phase or combination of phases, provided that the second phase is selected to be the time when the impact of the "ping" should be delivered to the heart. The systems and methods may predict when the second phase of the heartbeat cycle will begin based on previously monitored hemodynamic parameters (e.g., aortic pressure measured during the first phase of the heartbeat cycle). The second phase of the heartbeat cycle is predicted to take place over a second period of time. For example, the second period of time may be 0.05 seconds, 0.1 seconds, 0.2 seconds, 0.3 seconds, or any suitable length of time. The second period of time may be set to correspond to the length of the second phase of the heartbeat cycle for a particular patient. For example, if the second phase of the heartbeat cycle is a diastolic period, the second period of time may be set to the average diastolic time period for the particular patient, or may be set to a predicted length of the next occurring diastolic period. In some examples, the second period of time may be pre-set to a period of time less than that of a heartbeat. The second phase is predicted based on the monitored hemodynamic parameter and the identified first phase of the heartbeat cycle. A heartbeat signal may be monitored and, based on that monitored signal, the systems and methods predict when the next diastolic or systolic period will occur. By anticipating the timing of a heartbeat cycle phase, the systems and methods can then time an increase or decrease of the pump speed (the "ping") to accurately start (or so that its impact can be delivered) when the second phase of the heartbeat cycle starts. For example, systems and methods may be configured to ping the heart with a brief increase in pump output (e.g., by unloading the heart at a higher pump speed) so that the resulting increase in blood flow occurs simultaneously with the onset of a preferred point or period within the target heartbeat, for example at or momentarily after the onset of the dichrotic notch within a subsequent heartbeat, or mid-way through systole of the subsequent heartbeat, or during the entire diastolic period, or during a pre-determined portion of the subsequent heartbeat.

In certain implementations, the first phase of the heartbeat cycle is diastole of a first heartbeat and the second phase of the heartbeat cycle is diastole of a second immediately subsequent heartbeat. The first phase of the heartbeat cycle may be systole of a first heartbeat and the second phase of the heartbeat cycle is systole of a second heartbeat. In some implementations, the second phase is during a heartbeat that is multiple beats removed from the first heartbeat, while in other implementations the second phase is during an adjacent heartbeat to the first heartbeat.

After establishing the baseline and target heartbeat phases, the pump speed is then changed to ping the heart, for example by operating the pump during the second heartbeat at a second pump speed different than the first pump speed. The pump speed adjustment may be an increase or decrease in pump speed for pinging the heartbeat. For example, the pump may be adjusted so that the pump speed is briefly increased during a period of a heartbeat—e.g., during diastole of the heartbeat. The pump may also be adjusted so that the speed is returned to baseline or otherwise decreased during the same period of the heartbeat or at some other point during the same heartbeat. The pinging may also be configured to occur in reverse—by briefly decreasing the pump speed from a baseline.

Briefly changing the pump speed and returning to baseline results in the heart being momentarily "pinged," for example at a higher pump speed. In implementations, the heart pump operates at a first baseline pump speed, then changes momentarily to a higher second pump speed during a systolic or diastolic period (or other target period) of a subsequent heartbeat, and then quickly returns to the first pump speed. In some implementations, the change in pump speed lasts less than the length of a heartbeat, so that the pump returns to its baseline during the same heartbeat it is pinged. For example, the entirety of the ping may occur within the target heartbeat, such that the length of the ping is shorter in duration than the target heartbeat. Varying the pump speed within a single heartbeat reduces the influence of noise on the collection of hemodynamic data between the first and second phases, for improved accuracy.

The pump speed is adjusted so as to deliver the change in pump speed during the desired portion. For example, the change in speed may be delivered during systole, diastole, or both within a heartbeat. In implementations, to adjust the pump speed, a controller sends a signal to the pump to change the pump speed before the start of the target phase in time to account for any time delay between sending the control signal and the change in pump speed. The pump should deliver the actual increase or decrease in speed during the desired portion (e.g., diastole, at or after the dicrotic notch) of the target heartbeat. The ping is timed such that the increased pump speed occurs temporally during the course of a known period of the heartbeat. For example, the beginning of the speed ping may be synchronized with the start of diastole, the end of diastole, the start of systole, the end of systole, peak systolic pressure, or any other suitable time. The end of the speed ping may be synchronized with the start of diastole, the end of diastole, the start of systole, the end of systole, peak systolic pressure, or any other suitable time. In some implementations, the ping is achieved by increasing or decreasing the pump speed during a set period of time. For example, the ping may be synchronized with the start of diastole so that the ping occurs during diastole. Alternatively, the ping may be synchronized with the end of diastole so that the ping occurs during systole of a following heartbeat. In other adaptations, the ping is synchronized with the start of systole, the end of systole, peak systolic pressure, or any other suitable time. The ping is configured to last for a set period of time. In some adaptations, the ping is set to last for a period of time corresponding to the length of the phase of the heartbeat. For example, the ping may be set to last for about 0.05 seconds, 0.1 seconds, 0.2 seconds, 0.3 seconds or any other suitable length of time.

Pinging the heart or other vasculature by momentarily adjusting mechanical circulatory support (e.g., the pump speed) applies perturbations to the heart or other vasculature, which allows for the determination of systemic resistance, compliance and additional metrics of cardiac performance, including cardiac output. Such determinations can be done without introducing further hardware (beyond the pump providing hemodynamic support) into the patient's body (although such additional hardware could still be used, if desired). To make the determinations, a hemodynamic wave form (for example, the aortic (or ventricular) pressure waveform) during a regular heartbeat and a heartbeat that has been pinged is compared via a nonlinear model, such as a Windkessel model, described below. The changes in pressure waveforms (or other hemodynamic parameter) between the normal heartbeat and pinged heartbeat are reflected in differing values within the model during the two time periods (one time period for the baseline (normal) heartbeat and one for the target (pinged) heartbeat), creating two model equations. Knowing the pressure waveform for the two time periods allows the number of unknown variables between the two model equations to be reduced, such that resistance and compliance can be calculated. The total cardiac flow may then calculate using the calculated resistance and compliance values and the aortic pressure waveform by applying Equation (2):

$$C\frac{dP}{dt} + \frac{P}{R} = i_h + i_p \quad (2)$$

where C is the compliance, R is the resistance, P is the aortic pressure wave form, $i_h$ is the native cardiac flow, $i_p$ is the flow contributed by the pump, and $i_h+i_p$ is the total cardiac flow. CO may be calculated by taking the average of the total cardiac flow $i_h+i_p$ resulting from Equation (1) over a period of time (e.g., 5 seconds, 10 seconds, or 30 seconds). For example, the period of time may be the length of a single heartbeat, and the CO calculation may be presentative of CO during that heartbeat. In at least that respect, the systems and methods perform as a CO sensor for determining native cardiac output of the heart, based on the pinging techniques disclosed herein.

Adaptations of the techniques described above may be applied in various ways. In some implementations, the hemodynamic parameter is monitored during the second phase of a second heartbeat. For example, the heart pump system may continuously monitor aortic pressure or any other hemodynamic parameter. In some implementations, the monitored hemodynamic parameter during the first phase is compared to the monitored hemodynamic parameter during the second phase. For example, a first blood volume pumped by the heart during the first phase and a second blood volume pumped by the heart during the second phase may be calculated. A numerical difference between the first blood volume and the second blood volume may be calculated to quantifiably compare the hemodynamic parameter during the first phase to the second phase. For example, the area under the curve (AUC) of a flow curve may represent the blood volume. The difference in AUC during the first phase and during the second phase may be indicative of the difference in blood volume pumped at the first pump speed and second pump speed. Comparing the hemodynamic parameter between the first phase and the second phase may also include assessing linearity of the change in the hemodynamic parameter. For example, aortic pressure may not scale linearly between pump speeds, meaning the change in aortic pressure from one pump speed to the next may not be a linear progression. Depending on how the change in aortic pressure scales between pump speeds, the aortic pressure at different pump speeds may be predicted.

A metric indicative of cardiac performance of the heart may be computed based on the change in the hemodynamic parameter between the first phase and the second phase. For example, the metric indicative of cardiac performance may be determined from different pressure wave forms of the heart cycle during a first heartbeat and a second heartbeat; that metric may be systemic resistance, systemic compliance, CO, CPO, stroke volume, stroke work, ejection fraction, cardiac contractility, ventricular elastance, cardiac index, a prediction of patient survival. Many metrics indicative of cardiac performance are interrelated. For example, CO is determined based on the flow rate of the blood through an intravascular pump placed within a patient's heart. The stroke volume is an index of left ventricular function which formula SV=CO/HR, where SV is the stroke volume, CO is the cardiac output, and HR is the heart rate. Stroke work is the work done by the ventricle to eject a volume of blood and can be calculated from the stroke volume according to the equation SW=SV*MAP, where SW is the stroke work, SV is the stroke volume, and MAP is the mean arterial pressure. Cardiac work is calculated by the product of stroke work and heart rate. CPO is a measure of the heart function representing cardiac pumping ability in Watts. CPO is calculated using the cardiac power output equation, represented below by equation $$CPO = MAP * CO/451 \quad (3)$$

where CPO is the cardiac power output, MAP is the mean aortic pressure, CO is the cardiac output, and 451 is a constant used to convert mmHg×L/min into Watts. The ejection fraction can be calculated by dividing the stroke volume by the volume of blood in the ventricle. Other parameters, such as chamber pressure, preload state, afterload state, heart recovery, flow load state, variable volume load state, and/or heartbeat cycle flow state can be calculated from these values or determined via these parameters. In some implementations, the metric indicative of cardiac performance of the heart is computed via a two-element Windkessel model of the vascular system (e.g., the Windkessel model of FIG. 5) to model the dynamic and non-linear cardiac and vascular interactions. The process thus employs a time-variant non-linear model of the vascular system and uses the coupling between an intravascular blood pump device and a patient's hemodynamic function, a well-controlled analog to ventriculo-vascular coupling, to continuously determine systemic vascular resistance and compliance and quantify cardiac stroke volume without need for additional external measurements.

Operation of the pump may be adjusted based on the metric indicative of cardiac performance. Adjusting pump operation may include increasing pump speed, decreasing pump speed, adjusting pump placement, turning the pump off, or any other suitable adjustment. For example, if the metric indicative of cardiac performance is stroke volume, if the stroke volume is below a threshold, the pump speed may be increased, while if the stroke volume is above a threshold, the pump speed may be decreased.

In some implementations, a CO sensor is provided for determining the cardiac output of the patient's native heart. The CO sensor may include one or more hardware, software, and firmware elements configured to perform the methods described herein. In some implementations, the CO sensor includes a mechanical circulatory support device (e.g., an intravascular blood pump) with a pressure sensor and a processor configured to receive measurements from the pressure sensor and determine native cardiac output using intrabeat pinging, as described herein. The mechanical circulatory support device may be configured to be placed at least partially within a patient's heart. In some adaptations, the intravascular blood pump includes a cannula, a rotor configured to pump blood through the cannula, and a drive mechanism configured to impart power to turn the rotor. In some implementations, the cannula is configured to extend across the aortic valve such that the distal end of the cannula is within the left ventricle and the proximal end of the cannula is within the aorta. For example, the heart pump system may be considered "in position" when the cannula is placed across the aortic valve such that the blood inlet to the pump is within the left ventricle and the outlet from the pump is within the aorta. The drive mechanism may include an onboard motor, a drive cable, a drive shaft, or any other suitable element or combination thereof.

The CO sensor may include an elongate catheter body coupled to the cannula. The elongate catheter may include a drive cable, electrical wiring connecting the blood pump to a control system, any suitable element, or any combination thereof. In some implementations, the pump includes a pump housing and a motor housing coupled to the cannula at a distal end of the motor housing. The rotor may be rotated within the pump housing to induce a flow of blood into the cannula.

The CO sensor may include a hemodynamic parameter sensor operationally positioned at the blood pump (or proximal or distal to the blood pump) and configured to detect pressure within the blood vessel arising at least in part from the pumping of blood within the vessel. For example, the pressure sensor may be an optical sensor on or near the pump housing or cannula. As another example, the pressure sensor may comprise a pressure measurement lumen configured to measure aortic pressure. A differential pressure sensor may also be used, where one side or surface of the differential pressure sensor may be exposed to the aortic pressure, a second side or surface of the differential pressure sensor may be exposed to the ventricular pressure, and the differential pressure sensor may measure the difference between the aortic and ventricular pressures.

The CO sensor includes a controller electrically coupled to the pressure sensor and configured to detect signals from the sensor indicative of blood pressure. All or part of the controller may be in a controller unit separate/remote from the intravascular blood pump. In some implementations, the control system is internal to the intravascular blood pump.

The controller may be configured to calculate CO based on a non-linear model that correlates CO to vascular resistance and compliance, which are based on changes in hemodynamic values as a result of pinging the heart. For example, the non-linear model may be a Windkessel model, or a simplified Windkessel mode used in correlation with a heart pump system positioned across a patient's aortic valve. The governing equation for this model is:

$$C\frac{dP}{dt} + \frac{P}{R} = i_h + i_p \quad (2)$$

where C is compliance, P is aortic pressure, R is resistance, $i_h$ is flow from native heart operation and $i_p$ is flow from the pump. During diastole, the aortic valve is closed, so the only flow through the left ventricle comes from the action of the pump positioned across the valve. By discounting the heart current source and assuming pump flow as constant, the model can thus be simplified as follows:

$$P = P_0 e^{-\frac{t}{RC}} + i_p R \tag{4}$$

Resistance and compliance may be then determined via the following two equations, where P1 and P2 are pressure waveforms measured at different pump speeds (e.g., one at pinging, another either before or after pinging):

$$P_1 = P_{01} e^{-\frac{t}{RC}} + i_{p1} R \tag{5}$$

$$P_2 = P_{02} e^{-\frac{t}{RC}} + i_{p2} R \tag{6}$$

At low pump speeds, the pump flow $i_{p1}$, and therefore the $i_{p1}R$ term of Equation (5), may be approximated as zero, resulting in a simple exponential $$P_1 = P_{01} e^{-\frac{t}{RC}}$$

for Equation (5). Pump flow is determined by a range of factors including pump speed, the pressure differential between the aortic and the ventricular pressure, and the pump model. For example, for a particular pump model, when the pressure differential between aortic and ventricular pressure is around 40 to 50 mmHg and the pump speed is around 23,000 RPM, the pump flow is close to zero. At that pressure level (40 to 50 mmHg), when the speed is higher than 30,000 PRM, the flow should not be approximated as zero. After determining R using Equation (6) and the above simplification, the $i_{p1}R$ term may be added back to Equation (5) to then accurately determine C.

In some implementations, $P_0$ is assumed to be proportional to the reciprocal of the corresponding pump speed, such that $$\frac{P_{01}}{\text{speed}_2} = \frac{P_{02}}{\text{speed}_1}.$$

Therefore at t=0, Equations (5) and (6) become:

$$P_1(t=0) = P_{01} + i_{p1} R = \frac{\text{speed}_2 \times P_{02}}{\text{speed}_1} + i_{p1} R \tag{5a}$$

$$P_2(t=0) = P_{02} + i_{p2} R \tag{6a}$$

From Equations (5a) and (6a), R can be calculated as follows:

$$R = \frac{\text{speed}_2 \times P_2(t=0) - \text{speed}_1 \times P_1(t=0)}{i_{p2} \times \text{speed}_2 - i_{p1} \times \text{speed}_1} \tag{7}$$

where $P_1(t=0)$ and $P_2(t=0)$ are the measured initial aortic pressure at the beginning of diastole for a first heartbeat and a second heartbeat, respectively. For a desired period of time (e.g., 5 seconds, 10 seconds, 1 minute or any given period of time as desired), the total cardiac flow can then be calculated from Equation (3). Specifically, the CO, or the average cardiac flow over this desired time can be calculated as:

$$CO = \int_{t_{start}}^{t_{end}} \left( C\frac{dP}{dt} + \frac{P}{R} \right) dt = C \times (P(t = t_{end}) - P(t = t_{start})) + \int_{t_{start}}^{t_{end}} \left( \frac{P(t)}{R} \right) dt \tag{8}$$

where $t_{end}$ is equal to the end point of the desired time period and $t_{start}$ is equal to the start time of the desired time period. Because of the repetitiveness of the aortic pressure waveform, and if the desired time interval is long enough (for example, 10 seconds), the compliance term in the above equation $C \times (P(t=t_{end}) - P(t=t_{start}))$ may be close to zero or so much smaller than CO that it may be approximated as zero in Equation (8). CO may thus be calculated as:

$$CO = \int_{t_{start}}^{t_{end}} \left( \frac{P(t)}{R} \right) dt \tag{9}$$

CO is in turn equal to:

$$CO = \frac{MAP}{R} \tag{10}$$

where MAP is the mean arterial pressure within the desired time window from $t_{start}$ to $t_{end}$.

In some aspects, mechanical circulatory support may be provided to a patient using a blood pump, according to the systems and methods described herein. Providing mechanical circulatory support may include actuating the blood pump within the patient's vasculature, determining CO of the patient's heart using any of the systems and methods described herein, and adjusting the blood pump's pumping speed based on the determined CO.

In some aspects, mechanical circulatory support system may comprise an intracardiac blood pump having a cannula that is configured to extend within the left ventricle of a heart and a pressure sensor configured to detect the left ventricular end diastolic pressure. The system may be configured to determine CO according to any of the methods described herein.

In some implementations, a pump is placed within a patient's heart. The pump may be introduced to the patient because the patient is in cardiogenic shock, is receiving coronary intervention or having a heart attack, or is otherwise experiencing a decline in cardiac health. The pump may be positioned across the aortic valve such that a blood inlet to the pump is within the left ventricle and an outlet from the pump is within the aorta. The pump contributes to native heart operation such that CO from the heart is equal to native CO plus pump output.

A first aortic pressure wave may be detected. The first aortic pressure wave reflects a plurality of beats of the heart, each reflected beat including a dicrotic notch. The pressure waveform may be measured via a pressure sensor. In some implementations, the pressure sensor may be on-board the pump. In some implementations, the pressure sensor is located externally from the pump and receives fluid or electrical signals. The pressure sensor may communicate with a controller configured to control operation of the pump.

Hemodynamic support may be applied to the heart at a first pumping rate during a first beat of the plurality of beats. For example, the first pumping rate may be a first rotor speed, such as a P-level described above. The hemodynamic support to the heart is adjusted during a second beat of the plurality of beats by providing a second pumping rate to the heart during the second beat (e.g., during systole, after its dicrotic notch). The first pumping rate would be set to be different than the second pumping rate.

A second aortic pressure wave of the heart may be detected during the second beat. The second aortic pressure wave may be compared to a portion of the first aortic pressure wave corresponding to the second beat to detect a change in the second aortic pressure wave. In some examples, the second aortic pressure wave may be compared to the first aortic pressure wave by comparing the area under the curve (AUC) for a length of time represented by a portion of the second aortic pressure wave to the same length of time represented by a portion of the first aortic pressure wave. In some examples, global maxima and minima of the first and second aortic pressure waves may be compared. The shape or slope of the first and second aortic pressure waves may be compared, i.e., through the change in derivative of the waves over time. In some implementations, the first aortic pressure wave is compared to the second aortic pressure wave via a nonlinear model (e.g., a Windkessel model, described below). The differing waveforms provide two sets of values to the model, resulting in two different equations, one for each of the aortic pressure waveforms. The change between the first and second aortic pressure waves may be used to identify resistance and compliance of the systemic vasculature. Comparing the hemodynamic parameter between the first aortic pressure wave and the second aortic pressure wave may also include assessing linearity of the change in the aortic pressure wave between the first and second pump speed. For example, aortic pressure may not scale linearly between pump speeds, meaning the change in aortic pressure from one pump speed to the next may not be a linear progression. Depending on how the change in aortic pressure scales between pump speeds, the aortic pressure at different pump speeds may be predicted.

In some implementations, CO is determined based on a non-linear transfer function relating CO to systemic resistance and compliance. In some implementations, the non-linear transfer function includes a Windkessel model. In some implementations, the transfer function further relates to the aortic pressure waveform.

The systems and methods may compare the hemodynamic parameter during the first heartbeat to the hemodynamic parameter during the second heartbeat to calculate a change in the hemodynamic parameter between the first heartbeat and the second heartbeat. The change is at least partially caused by the difference between the first and second output levels of the mechanical circulatory support device. For example, if the hemodynamic parameter is aortic pressure, increasing the device's output level will increase measured aortic pressure and decreasing the output level will decrease measured aortic pressure. This change in aortic pressure from the first pump output level to the second pump output level indicates the mechanical circulatory support device's contribution to the aortic pressure change.

A metric indicative of vascular and/or cardiac performance of the heart may be computed based on the change in the hemodynamic parameter between the first heartbeat and the second heartbeat. For example, the hemodynamic parameter during the first heartbeat and the second heartbeat may be compared via a nonlinear model, such as a Windkessel model, described below. The changes in hemodynamic parameter between the normal heartbeat and pinged heartbeat are reflected in differing values within the model during the two time periods (one time period for the first heartbeat and one for the second heartbeat), and two model equations may therefore be used to determine the cardiac performance. In some implementations, the metric indicative of cardiac performance is cardiac output. To calculate cardiac output, vascular resistance and compliance may be determined based on the change in the hemodynamic parameter between the first heartbeat and the second heartbeat, as described above. Knowing the hemodynamic parameter waveform for the two time periods allows the number of unknown variables between the two model equations to be reduced, such that resistance and compliance (and ultimately cardiac output) can be calculated.

In some implementations, the systems and methods described herein include modeling a patient's heartbeat to represent the heartbeat as a series of sinusoids that can be used by the processor to construct one or more heartbeats representative of the patient's heart function. The constructed heartbeat(s) is then used by the processor to adjust the pump speed. As described above, the blood pump is operated at a first pump speed (or other operating parameter) and is then adjusted to a second pump speed (or other operating parameter) to ping the heart, and then quickly reduced to the baseline first speed or parameter. A hemodynamic parameter (e.g., aortic pressure) is monitored during the pump operation, including during the pinging period. The processor calculates a metric indicative of cardiac performance of the heart, based on (i) the first operating parameter (pump speed), (ii) the second operating parameter (e.g., pump speed during pinging), and (iii) the hemodynamic parameter during first and second periods, e.g., during the first diastolic period and the second diastolic period. The metrics are used in a transfer function or set of equations such as those described above in relation to the Windkessel model. A mathematical representation of the hemodynamic parameter is determined by the controller processor for the first and second diastolic periods. For example, the mathematical representation may be a summation of sinusoids or other wave form function indicative of the hemodynamic parameter at a given pump speed.

Cardiac performance is then computed by the processor from the sinusoid summation or other wave forms. The computation may include deconstructing a first waveform representative of the hemodynamic parameter for the first diastolic period (with the pump operating at a first pump speed) to determine a first set of sinusoids, and deconstructing a second waveform representative of the hemodynamic parameter for the second diastolic period (with the pump operating at a second pump speed) to determine a second set of sinusoids. These deconstructions include applying a Fourier transform to the first waveform, the second waveform, or both. A set of sinusoids may include one or more sinusoids summed together.

As the blood flow within the aorta is equal to the pump contribution ($i_p$) plus the native heart contribution ($i_h$), the first set of sinusoids and the second set of sinusoids may be compared to determine the contribution of the patient's heart ($i_h$) to blood flow within the aorta. For example, if the hemodynamic parameter is aortic pressure, it may be expressed as a summation of sinusoids resulting from the Fourier transform, as $$P = \sum_{n=1}^{N} A_n \sin(f_n t + \theta_n)$$

where P is the aortic pressure, $f_n$ is a frequency associated with a pump speed or other operating parameter, and $A_n$ and $\theta_n$ are coefficients for the operating parameter. Changing the operating parameter will change the sinusoids. The difference in the sets of sinusoids between operating parameters may be used to calculate the difference in flow from the changed operating parameters because the change in pressure between operating parameters will be proportional to the change in flow. In some implementations, the Fourier transform may be calculated for each pump speed in a range of pump speeds. In some implementations, patient response to the "pinged" pump speed may be minimal due to the limits on speed changes in a short period of time (i.e., the time it takes to ramp up a pump to an increased speed or slow down the pump to a decreased speed).

Decomposing the hemodynamic parameter over time into its constituent frequencies, resulting from changes in the operating parameter of the device, allows the hemodynamic parameter to be characterized using a complex mathematical equation or set of equations. In some implementation, the mathematical representation is an exponential equation based on the comparison of sinusoids. After the hemodynamic parameter waveform has been characterized by a mathematical equation, heart parameters such as vascular resistance and compliance may be determined from the equation. For example, if the hemodynamic parameter wave form is characterized as a series of exponential functions in the form of $$P = Ae^{\frac{-t}{B}} + D$$

(where B is equal to R*C and D is equal to $i_p$*C, P is pressure, R is systemic resistance, and C is systemic compliance), then systemic resistance and compliance values may be calculated by solving a system of equations with these coefficients for at least three points in time (i.e., with three known pressure measurements corresponding to three known pump operating parameters).

A heartbeat representative of the patient's heart function may be simulated based on the comparison of sinusoids indicative of incremental changes in hemodynamic parameters arising from changes in the pump operating parameters. For example, the blood pump may be operated at a range of pump speeds (e.g., P-1, P-2, P-3, P-4, etc.) where each pump speed corresponds to a rate of rotation of a rotor within the pump and analogous frequency (e.g., 100 Hz, 200 Hz, 300 Hz, 400 Hz, 500 Hz, 1000 Hz, 2000 Hz, 3000 Hz, etc.). Changing the pump speed (or frequency) will change the value of the hemodynamic parameter because it will change the flow of blood in the vasculature provided by the pump's operation. By gradually stepping through multiple pump speeds (or operating parameters, such as blood flow provided by the pump) to identify corresponding changes to one or more hemodynamic parameters, forming a hemodynamic waveform, and deconstructing the hemodynamic waveform resulting from each pump speed, a relationship between pressure and flow during diastole is established. The patient's overall heart function can then be mapped as a mathematical representation (as a function of the measured hemodynamic parameters) that can be used to simulate future heart function and inform delivery and control of mechanical circulatory support to the patient. For example, the measured aortic pressure waveform of any recorded heartbeat may be constructed using the methods described below—allowing the CO to be calculated for that heartbeat.

As described above, in some implementations, a brief change in pump speed can be applied to the pump within one heartbeat. This change in pump speed may be considered as an impulse stimulus. The aortic pressure recorded for this heartbeat may be compared to the aortic pressure of a heartbeat without this brief speed change or impulse stimulus. The difference of the two (the aortic pressure of the altered heartbeat and the aortic pressure of a "normal" heartbeat) may be considered the impulse response of the aortic pressure:

$$\Delta p(t) = p_1(t) - p_2(t)$$

where $P_1(t)$ is the pressure waveform measured with the impulse stimulus, $P_2(t)$ is the pressure waveform without the impulse stimulus, and $\Delta P(t)$ is the impulse response of the aortic pressure.

If this impulse stimulus is only applied during diastole, then the difference in the total cardiac flow for the two heartbeats can be represented as:

$$\Delta i(t) = i_1(t) - i_2(t)$$

where $i_1(t)$ and $i_2(t)$ are the pump flow for the heartbeat with the impulse stimulus and the heartbeat without the impulse stimulus, respectively, and $\Delta i(t)$ is the impulse response of the cardiac flow.

Then the aortic pressure vs. pump flow relationship can be estimated in frequency domain as:

$$H(f) = \frac{\Delta P(f)}{\Delta I(f)}$$

where $\Delta P(f)$ is frequency domain representation (e.g., Fast Fourier Transform or FFT) of $\Delta p(t)$, $\Delta I(f)$ is the frequency domain representation of $\Delta i(t)$, and H(f) is the frequency domain transfer function for the aortic pressure versus pump flow relationship.

Once this relationship H(f) is established as outlined above, the total cardiac flow for any heartbeat with aortic pressure measured as p(t), can be calculated as:

$$\text{total\_i}(t) = IFFT\left(\frac{P(f)}{H(f)}\right)$$

where P(f) is the frequency domain representation of p(t) and IFFT is the Inverse Fast Fourier Transform.

DETAILED DESCRIPTION

Figure 1:
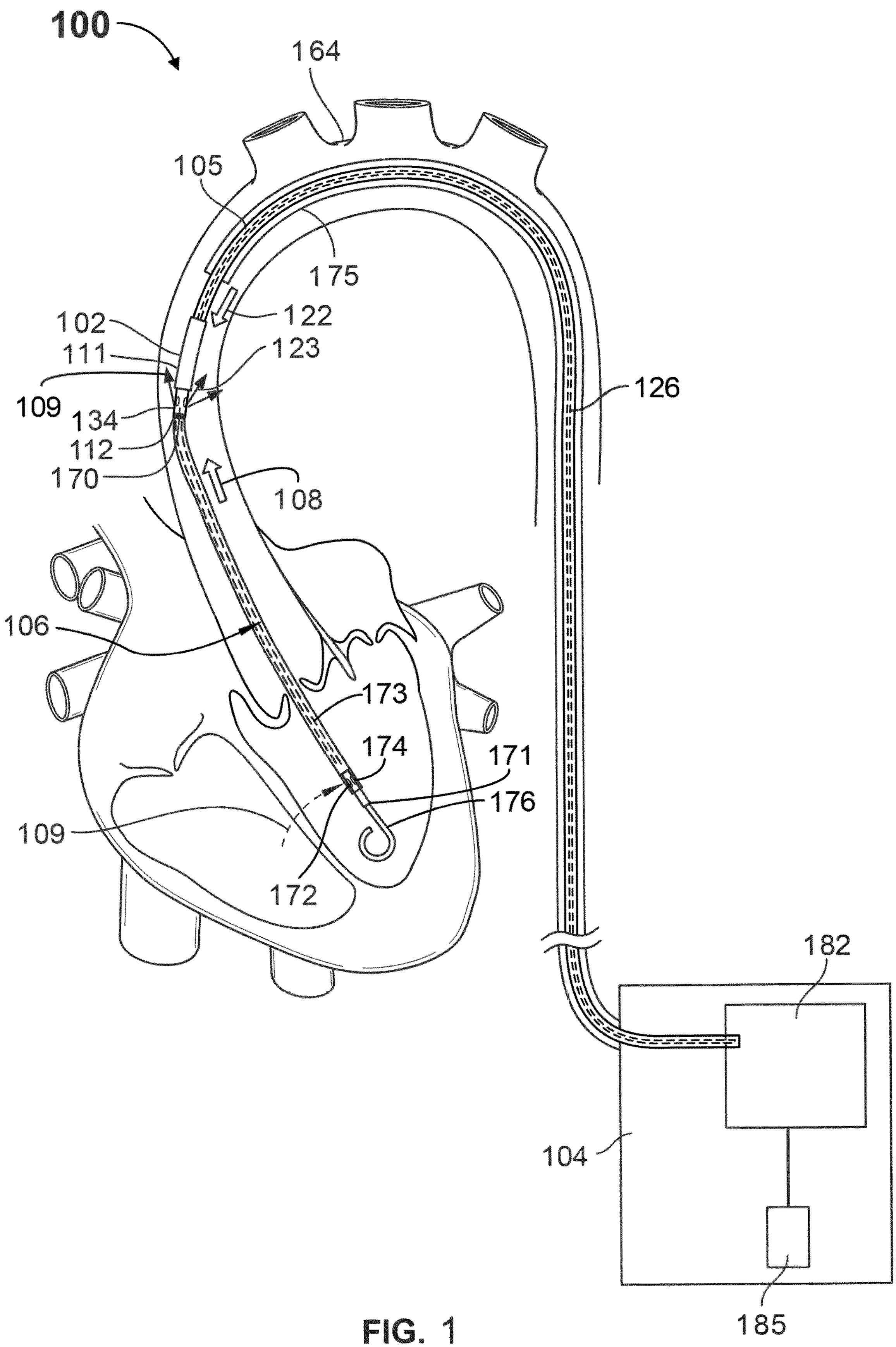
FIG. 1 show an illustrative heart pump system inserted into a blood vessel of a patient.

To provide an overall understanding of the systems, methods, and devices describe herein, certain illustrative embodiments will be described. Although the embodiments and features described herein are specifically described for use in connection with a percutaneous heart pump system, it will be understood that the components and other features outlined below may be combined with one another in any suitable manner and adapted and applied to other types of cardiac therapy and heart pump systems, including heart pump systems implanted using a surgical incision, intra-aortic pumps, and the like.

The systems, devices, and methods described herein enable a support device residing completely or partially within an organ to assess that organ's function. In particular, the systems, devices, and methods enable heart pump systems, such as percutaneous ventricular assist devices, to be used to assess the function of the heart. For example, such devices may be used in the treatment of cardiogenic shock.

Assessing the function of the heart using a heart pump system can alert health professionals to changes in cardiac function and allow the profession to tailor the degree of/level of support provided by the assist device (i.e., flow rate of blood pumped by the device) based on a particular patient's needs. For example, the degree of support can be increased when a patient's heart function is deteriorating, or the degree of support can be decreased when a patient's heart function is recovering and returning to a baseline of normal heart function. This can allow the device to dynamically respond to changes in heart function to promote heart recovery and can allow the patient to be gradually weaned off of the therapy. Furthermore, assessment of the heart function can indicate when it is appropriate to terminate use of the heart pump system. Although some embodiments presented herein are directed to heart pump systems implanted across the aortic valve and residing partially in the left ventricle, the concepts can be applied to devices in other regions of the heart, the cardiovascular system, or the body.

Assessment of cardiac function may include leveraging heart-device interactions to determine heart parameters. Using a Windkessel model of the vascular system to improve on traditional linear approximations and provide for dynamic variation of the vascular response, the systems and methods described herein introduce controlled perturbations of the vascular system through a heart pump system and, in response, calculate heart parameters such as stroke volume, vascular resistance and compliance, CO and left ventricular end diastolic pressure. In particular, the systems, devices, and methods described herein "ping" a heartbeat using a mechanical circulatory support system. "Pinging" comprises increasing the pump speed of the heart pump system for a time period, for example within a single heartbeat, thereby generating a spike in aortic pressure and flow. During the ping a hemodynamic parameter is altered and can be detected and compared to the hemodynamic parameter at another time (i.e., when the heart pump system is not being pinged) to calculate other hemodynamic parameters or otherwise measure cardiac performance.

Continuous measurement of vascular and cardiac performance by using the effects of a heart pump system can provide additional clinical data to aid in titration of appropriate device support. The systems and methods also provide for the use of device-arterial coupling to determine cardiac and vascular state, including the determination of native cardiac output. The mechanical circulatory support systems presented herein reside within the heart and work in parallel with native ventricular function. This allows the systems to be sensitive enough to detect native ventricular function unlike some more invasive devices. Thus, the systems, devices, and methods enable the use of mechanical circulatory support systems not only as support devices, but also as diagnostic and prognostic tools. The heart pump systems can function as sensors that extract information about cardiac function by hydraulically coupling with the heart. In some implementations, the heart pump systems operate at a constant level (e.g., constant rotational speed of a rotor), while power delivered to the assist device is measured. In certain implementations, the speed of the rotor of the heart pump system may be varied (e.g., as a delta, step, or ramp function) to further probe the native heart function.

FIG. 1 shows an illustrative heart pump system inserted into a blood vessel of a patient. As an example, heart pump systems compatible with the present disclosure are disclosed in U.S. Patent Application Publication No. 2018-0078159-A1, the contents of which are hereby incorporated by reference in their entirety. Generally, any other heart pump system or other mechanical circulatory support system (and sensor for obtaining physiological data from a patient) may be used with the present disclosure. In some implementations, the systems and methods described herein may use expandable pumps (e.g., Heartmate PUP™ family of devices (Thoratec Corporation)) or left atrium-to-femoral artery bypass pumps (e.g., TandemHeart family of devices (LivaNova, PLC)). In some implementations, the systems and methods described herein may use the IMPELLA® family of devices (Abiomed, Inc., Danvers MA).

The heart pump system 100 may operate within a heart, partially within the heart, outside the heart, partially outside the heart, partially outside the vascular system, or in any other suitable location in a patient's vascular system. The heart pump system may be considered "in position" when cannula 173 is placed across the aortic valve such that a blood inlet (e.g., blood inlet 172) to the pump is within the left ventricle and an outlet (e.g., outlet openings 170) from the pump is within the aorta. The heart pump system 100 includes a heart pump 106 and a control system 104. All or part of the control system 104 may be in a controller unit separate/remote from the heart pump 106. In some implementations, the control system 104 is internal to the heart pump 106. The control system 104 and the heart pump 106 are not shown to scale. The pump system 100 includes an elongate catheter body 105, a motor housing 102 and a drive shaft in which a pump element is formed. The pump 100 includes a pump housing 134, and a motor housing 102 coupled to a cannula 173 at a distal end 111 of the motor housing 102. An impeller blade on the drive shaft may be rotated within a pump housing 134 to induce a flow of blood into the cannula 173 at a suction head 174. The suction head 174 provides a blood inlet 172 at the distal end portion 171 of the cannula 173. The flow 109 of blood passes through the cannula 173 in a first direction 108 and exits the cannula 173 at one or more outlet openings 170 of the cannula 173.

The rotation of the drive shaft within the pump housing 134 rotates a pump element within a bearing gap. A hemocompatible fluid is delivered through the elongate catheter 105 through the motor housing 102 to a proximal end portion of the cannula 173 where the fluid lubricates the pump. The flow of hemocompatible fluid has a second direction 122 through the bearing gap of the pump. After exiting the bearing gap, the hemocompatible fluid follows flow direction 123 and becomes entrained in the flow of blood and flows into the aorta with the blood.

The heart pump 100 is inserted into a vessel of the patient through a sheath 175. The pump housing 134 encloses the rotor and internal bearings and may be sized for percutaneous insertion into a vessel of a patient. In some implementations, the pump is advanced through the vasculature and over the aortic arch 164. Although the pump is shown in the left ventricle, the pump may alternatively be placed in the right heart, such that the blood is pumped from the patient's inferior vena cava or right atrium, through the right ventricle into the pulmonary artery.

A flexible projection 176 is included at a distal end portion 171 of the cannula 173, distal to the suction head 174, in order to stabilize the heart pump 100 in a vessel or chamber of the heart. The flexible projection 176 is atraumatic and helps prevent the suction head 174 from approaching the wall of the vessel where it may become stuck due to suction. The flexible projection 176 extends the pump 100 mechanically, but not hydraulically, as the flexible projection 176 is non-sucking. In some implementations, the flexible projection may be formed as a pigtail. In some aspects, the pump need not include a flexible projection.

The elongate catheter 105 houses a connection 126 with a fluid supply line and electrical connection cables. The connection 126 also supplies a hemocompatible fluid to the pump from a fluid reservoir and is contained within control system 104.

The control system 104 includes controller 182 that controls pump 106 by delivering power to the motor and controlling the motor speed. The control system 104 includes circuitry for monitoring the motor current for drops in current indicating air in the line, changes in differential pressure signal, flow position, suction, or any other suitable measurement. In some implementations, the control system 104 includes display screens to show measurements such as differential pressure signal and motor current. The control system 104 may include warning sounds, lights or indicators to alert an operator of sensor failures, disconnects or breaks in the connection 126, or sudden changes to patient health.

The motor 108 is configured to operate at a speed required to maintain the rotor at a set speed. As a result and as further described below, the motor current drawn by the motor to maintain the rotor speed can be monitored and used to understand the underlying cardiac state. The control system 104 is configured to alter the speed of the pump within a heartbeat cycle of the assisted heart, resulting in a change of the blood flow through the pump, the speed alteration of which is synchronized with the heartbeat by means of at least one event per heartbeat cycle which is related to a predetermined event in the heartbeat cycle—i.e., the systems, devices, and methods described herein "ping" a heartbeat using the heart pump system. "Pinging" occurs then the pump speed of the heart pump system (or other mechanical circulatory support device) is increased or decreased for a relatively short period of time, e.g., during a phase of a heartbeat cycle, and then changed to baseline or another speed. The pump speed may be increased for a period of time within a single heartbeat or across multiple heartbeats.

Figure 3:
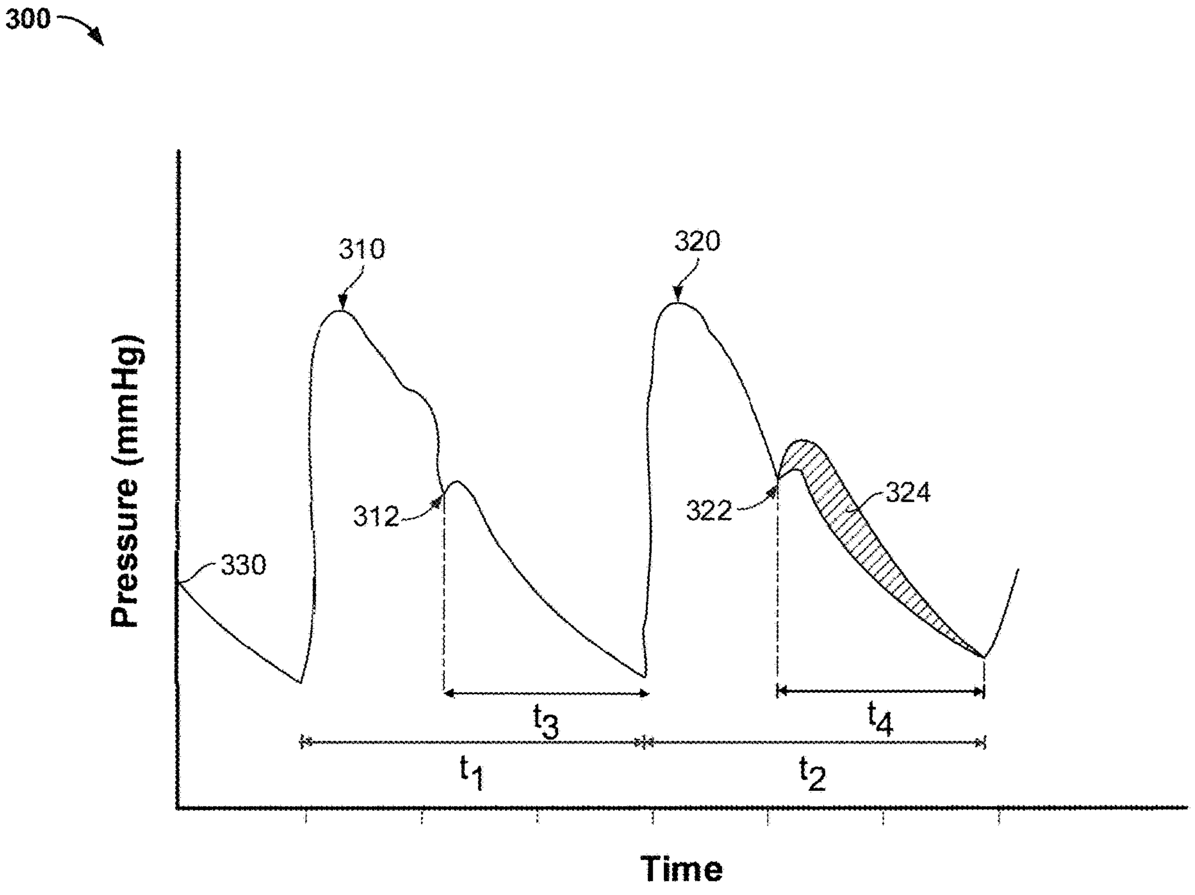
FIG. 3 shows a plot 300 of pressure versus time for a heart pump system according to certain implementations.

The heart pump may operate at a variety of pump speeds or P-levels. P-level is the performance level of the heart pump system and related to flow control of the system. As P-level increases, the flow rate, motor current, and revolutions per minute associated with the heart pump system increase; thus, higher P-levels correspond to higher flow rates and revolutions per minute associated with the heart pump system. For example, power level P-1 may correspond to a first number of rotations per minute (RPM) for the rotor, while power level P-2 corresponds to a second number of RPM. In some examples, the pump operates at ten different power levels ranging from P-0 through P-9. These P-levels may correspond to 0 RPM through 100,000 RPM or any suitable number. Changing the speed of the rotor changes the CO of the heart, as shown in FIG. 3 and described below.

In some implementations, the pump speed is increased during systole, diastole, or both within a single heartbeat. The ping is timed such that the increased pump speed occurs for a known period of the heartbeat. For example, the beginning of the speed ping may be synchronized with the start of diastole, the end of diastole, the start of systole, the end of systole, peak systolic pressure, or any other suitable time. The end of the speed ping may be synchronized with the start of diastole, the end of diastole, the start of systole, the end of systole, peak systolic pressure, or any other suitable time. In some implementations, the pump speed is increased or decreased for a set period of time. For example, the start of the ping may be synchronized with the start of diastole, at or after the dicrotic notch, with the end of diastole, the start of systole, the end of systole, peak systolic pressure, or any other suitable time. The ping may last for a set period of time. For example, the ping may last for 0.05 seconds, 0.1 seconds, 0.2 seconds, 0.3 seconds or any other suitable length of time.

The control system 104 includes a current sensor (not shown). The controller 182 supplies current to the motor 108 by the connection 126 such as through one or more electrical wires. The current supplied to the motor 108 via the connection 126 is measured by the current sensor. The load that the motor of a mechanical pump experiences corresponds to the force of the pressure head, or the difference between the aortic and left ventricular pressure. The heart pump 106 experiences a nominal load during steady state operation for a given pressure head, and variations from this nominal load are a result of changing external load conditions, for example the dynamics of left ventricular contraction. Changes to the dynamic load conditions alter the motor current required to operate the pump rotor at a constant, or substantially constant, speed. As described above, the motor may operate at a speed required to maintain the rotor at a set speed, and the motor current drawn by the motor to maintain the rotor speed can be monitored and used to detect the underlying cardiac state. The cardiac state can be precisely quantified and understood by simultaneously monitoring the pressure head during the heartbeat cycle using a pressure sensor 112. The heart parameter estimator 185 receives current signals from the current sensor as well as pressure signals from the pressure sensor 112. The heart parameter estimator 185 uses these current and pressure signals to characterize the heart's function. The heart parameter estimator 185 may access stored look-up tables to obtain additional information to characterize the heart's function based on the pressure and current signals. For example, the heart parameter estimator 185 may receive an aortic pressure from the pressure sensor 112, and using look-up tables, may use the aortic pressure to determine a delta pressure. Heart parameter estimator 185 may be software programmed in controller 182, or may be separate hardware connected to controller 182 by a wired or wireless connection. Heart parameter estimator 185 is configured to execute the algorithms described herein. For example, heart parameter estimator 185 may be configured to estimate pump flow based on current delivered to the pump, and may be configured to determine native cardiac output according to the methods described herein.

Various implementations of pressure sensors may be used. One example is an optical sensor, or a differential sensor. The differential pressure sensor is a flexible membrane integrated into the cannula 173. One side of the sensor is exposed to the blood pressure on the outside of the cannula and the other side is exposed to the pressure of the blood inside of the cannula. The sensor generates an electrical signal (the differential pressure signal) proportional to the difference between the pressure outside the cannula and the pressure inside, which may be displayed by the heart pump system. When the heart pump system is placed in the correct position across the aortic valve, the top (outer surface) of the sensor is exposed to the aortic pressure and the bottom (inner surface) of the sensor is exposed to the ventricular pressure. Therefore, the differential pressure signal is approximately equal to the difference between the aortic pressure and the ventricular pressure. Other sensors, such as an optical sensor or a fluid filled column, may be used.

Figure 2:
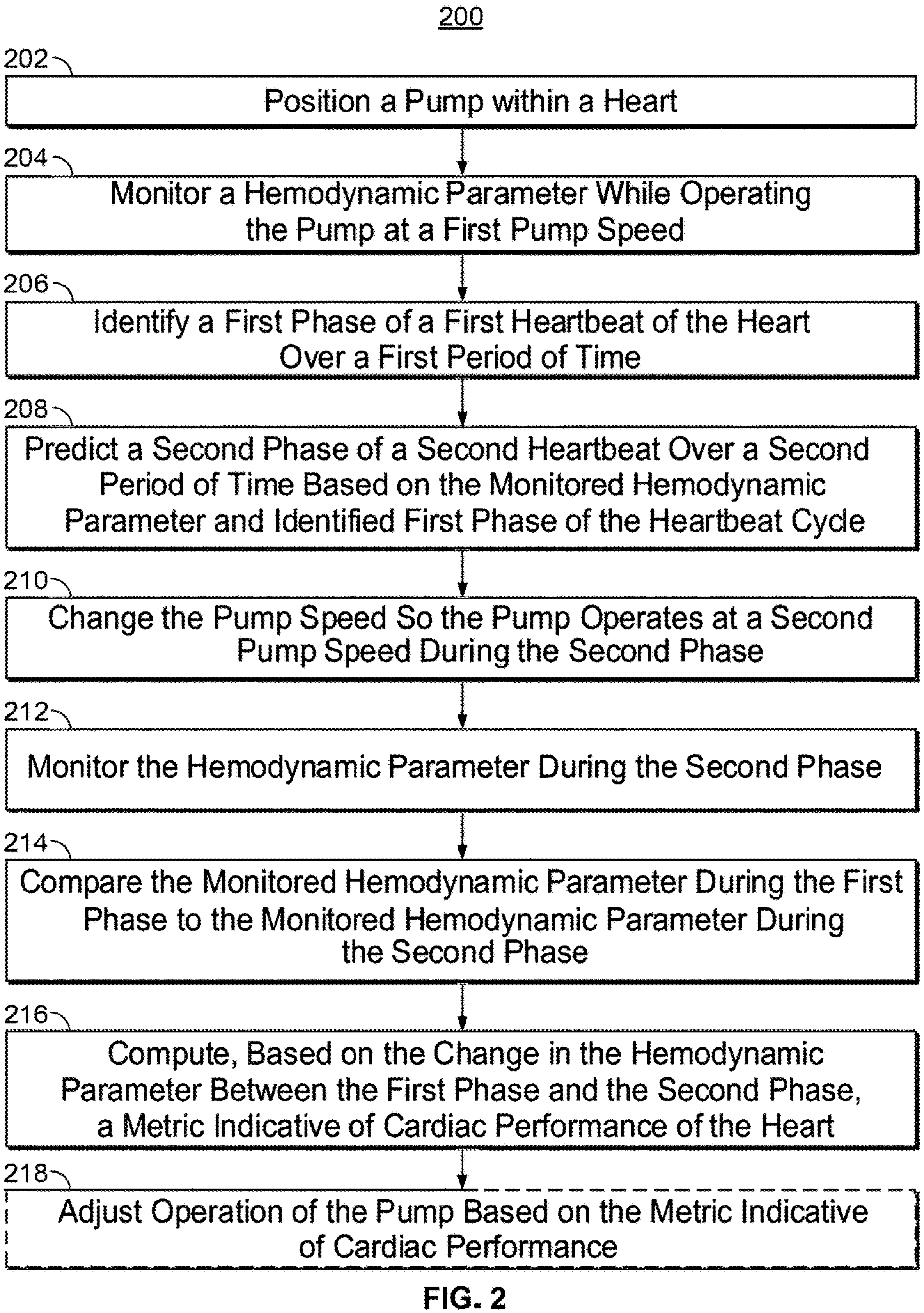
FIG. 2 illustrates a process for computing a metric indicative of cardiac performance of the heart according to certain implementations.

FIG. 2 illustrates a process 200 for determining cardiac performance of the heart. The process includes a series of steps relating to altering the operation of a pump (e.g. pinging) within a patient's heart in order to compare monitored hemodynamic parameters and thus compute a metric indicative of cardiac performance of the heart (e.g., CO). For example, the process described below may increase the speed of a pump for a short period of time, then compare the aortic pressure during the time of the increased pump speed to aortic pressure during normal pump operation to calculate or characterize vascular resistance or compliance, which may be used to determine CO and/or alter operation of the pump to better treat the patient. Vascular resistance or compliance is determined through a Windkessel model (as described in FIG. 5 below) or other non-linear time dependent model by building a system of two equations, one each for normal operation of the pump and increased speed operation of the pump, which can be solved using measured or estimated pressure and flow values to calculate resistance and compliance values for the systemic vasculature. The process 200 can be performed using the heart pump system 100 of FIG. 1 or any other suitable mechanical circulatory support system.

In step 202, a pump (e.g., pump 106 of FIG. 1) is positioned within a patient's heart. In some implementations, the pump is an intravascular blood pump device placed within the patient's heart via percutaneous insertion. In some implementations, the pump may be a surgically implanted device, a left ventricular assist device, a counterpulsation device, an expandable heart pump, or any other suitable device. The pump may be introduced to the patient because the patient is in cardiogenic shock or otherwise experiencing a decline in health. The pump may be positioned across the aortic valve such that a blood inlet (e.g., blood inlet 172 of FIG. 1) to the pump is within the left ventricle and an outlet (e.g., outlet openings 170 of FIG. 1) from the pump is within the aorta.

The pump contributes to native heart operation such that:

$$CO = i_h + i_p \tag{1}$$

where CO is total cardiac output, $i_h$ is native cardiac output, and $i_p$ is flow contributed by the pump.

In step 204, a hemodynamic parameter is monitored while operating the pump at a first pump speed. A hemodynamic parameter may be any parameter relating to the flow of blood within the body. For example, the hemodynamic parameter may include at least one of heart rate, blood pressure, arterial oxygen saturation, mixed venous saturation, central venous oxygen saturation, arterial blood pressure, mean arterial pressure, right arterial pressure, central venous pressure, right ventricular pressure, pulmonary artery pressure, mean pulmonary artery pressure, pulmonary artery occlusion pressure, left atrial pressure, aortic pressure, differential pressure, left ventricular end pressure, stroke volume, stroke volume index, stroke volume variation, systemic vascular resistance, systemic vascular resistance index, pulmonary vascular resistance, pulmonary vascular resistance index, pulmonary vascular resistance, pulmonary vascular resistance index, left ventricular stroke work, left ventricular stoke work index, right ventricular stroke work, right ventricular stroke work index, coronary artery perfusion pressure, right ventricular end diastolic volume, right ventricular end diastolic volume index, right ventricular end systolic volume, right ventricular ejection fraction, arterial oxygen content, venous oxygen content, arterial-venous oxygen content difference, oxygen delivery, oxygen delivery index, oxygen consumption, oxygen consumption index, oxygen extraction ration, oxygen extraction index, total peripheral resistance, CO, cardiac index, and CPO. A pump speed is the speed of operation of the pump and corresponds to the amount of blood flow provided by the pump's operation. In some implementations, the pump speed may correspond to a speed of rotation of a rotor. For example, the pump speed may be 10,000 RPM, 20,000 RPM, 30,000 RPM, 40,000 RPM, 50,000 RPM, 60,000 RPM, 70,000 RPM, 80,000 RPM, 90,000 RPM, 100,000 RPM, or any suitable speed. A pump speed may correspond to a power level, or P-level, as described above in relation to FIG. 1. For example, the pump speed may be P-1, P-2, P-3, P-4, P-5, P-6, P-7, P-8, P-9, or any other suitable value. In some implementations, the pump speed may instead correspond to the rate at which a chamber of the pump fills up with and releases blood.

In step 206, a first phase of a first heartbeat of the heart is identified. For example, the first phase may be a systolic period, a diastolic period, or any other suitable phase. The first phase of the first heartbeat is identified from the shape of a hemodynamic parameter waveform. For example, the hemodynamic parameter may be aortic pressure. Process 200 includes identifying local minimum values in the aortic pressure waveform and determining a dicrotic notch, the start of dicrotic notch indicating the start of diastole, from the local minimum values. The first phase of the first heartbeat takes place during a first period of time. For example, the first period of time may be 0.05 seconds, 0.1 seconds, 0.2 seconds, 0.3 seconds, or any suitable length of time.

In step 208, a second phase of a second heartbeat is predicted based on the monitored hemodynamic parameter. For example, the second phase may be a systolic period, a diastolic period, or any other suitable phase; the second phase may be the same phase as the first phase (e.g., diastole). The second phase is predicted by monitoring the hemodynamic parameter over time and determining patterns in the hemodynamic parameter to anticipate when the second phase of the heartbeat cycle will begin. In some implementations, the second phase prediction may be further based on the identified first phase of the heartbeat cycle. For example, if the first phase is diastole of a first heartbeat and the second phase is diastole of a second heartbeat immediately after the first heartbeat, the second phase may be anticipated by determining the average length of a heartbeat and calculating the start of the second phase by adding the length of the heartbeat to the start time of the first phase. The second phase of the second heartbeat takes place over a second period of time. For example, the second period of time may be 0.05 seconds, 0.1 seconds, 0.2 seconds, 0.3 seconds, or any suitable length of time. By estimating when the second heartbeat (and subsequent heartbeats) will start, the system can time the change in pump speed so that its effects (e.g., increased flow from the left ventricle, increased aortic pressure) occur during a desired second phase of the second heartbeat.

In an example, the first phase is diastole of a first heartbeat and the second phase is diastole of a second heartbeat. In another example, the first phase is systole of a first heartbeat and the second phase is systole of a second heartbeat. In an example, the first phase is diastole of a first heartbeat and the second phase is systole of the first heartbeat.

In step 210, the pump speed is changed so the pump operates at a second pump speed during the second phase of the heartbeat cycle, to "ping" the heartbeat during that second phase. The pump speed may be increased or decreased. As shown in FIG. 3 and described below, the pump speed may be increased during a diastolic period—i.e., the first phase may be systole of a first heartbeat and the second phase may be diastole of the first heartbeat. To effect the change in pump speed, a controller (e.g., controller 104 of FIG. 1) may send a signal to the pump to change the pump speed before the start of the second phase so that the pump speed change happens during the second phase, to account for any time delay between sending the signal and the physical change in the pump speed. Varying the pump speed within a single heartbeat ensures there is little to no noise or outside factors affecting collection of hemodynamic data between the first and second phases.

After the "ping," the pump speed changes. In some implementations, the pump speed is changed back to the first pump speed after the second phase of the second heartbeat. For example, the heart pump may operate at the second pump speed only during a systolic or diastolic period before returning back to the first pump speed at or during that period.

In step 212, the hemodynamic parameter is monitored during the second phase of the second heartbeat while the pinging occurs. For example, the heart pump system may continuously monitor aortic pressure or any other hemodynamic parameter. In step 214, the monitored hemodynamic parameter during the first phase is compared to the monitored hemodynamic parameter during the second phase. For example, a first blood volume pumped by the heart during the first phase and a second blood volume pumped by the heart during the second phase may be calculated. A numerical difference between the first blood volume and the second blood volume may be calculated to quantifiably compare the hemodynamic parameter during the first phase of the first heartbeat to the second phase of the second heartbeat.

In step 216, a metric indicative of cardiac performance of the heart is computed based on the change in the hemodynamic parameter between the first phase and the second phase. For example, the metric indicative of cardiac performance may be systemic resistance, cardiac compliance, CO, CPO, stroke volume, stroke work, ejection fraction, cardiac contractility, ventricular elastance, cardiac index, a prediction of patient survival. For example, a numerical difference between a first blood volume pumped by the heart during the first phase of the heartbeat cycle and a second blood volume pumped by the heart during the second phase of the heartbeat cycle may be calculated. The numerical difference in blood volume may be used to determine stroke volumes for individual heartbeats or the average cardiac flow (CO) over a desired period of time. Many metrics indicative of cardiac performance are interrelated. For example, CO is determined based on the flow rate of the blood through and past the pump. The stroke volume is an index of left ventricular function which formula SV=CO/HR, where SV is the stroke volume, CO is the cardiac output, and HR is the heart rate. Stroke work is the work done by the ventricle to eject a volume of blood and can be calculated from the stroke volume according to the equation SW=SV*MAP, where SW is the stroke work, SV is the stroke volume, and MAP is the mean arterial pressure. Cardiac work is calculated by the product of stroke work and heart rate. CPO is a measure of the heart function representing cardiac pumping ability in Watts. CPO is calculated using the equation CPO=mAoP*CO/451, where CPO is the cardiac power output, mAoP is the mean aortic pressure, CO is the cardiac output, and 451 is a constant used to convert mmHg×L/min into Watts. The ejection fraction can be calculated by dividing the stroke volume by the volume of blood in the ventricle. Other parameters, such as chamber pressure, preload state, afterload state, heart recovery, flow load state, variable volume load state, and/or heartbeat cycle flow state can be calculated from these values or determined via these parameters. In some implementations, the metric indicative of cardiac performance of the heart is computed via a two-element Windkessel model of the vascular system (e.g., the Windkessel model of FIG. 5) to model the dynamic and non-linear cardiac and vascular interactions. The process thus employs a time-variant non-linear model of the vascular system and exploits device-arterial coupling, a well-controlled analog to ventriculo-vascular coupling, to continuously determine systemic vascular resistance and compliance and quantify cardiac stroke volume without need for additional external measurements.

In optional step 218, operation of the pump is adjusted, based on the metric indicative of cardiac performance. In some implementations, the pump speed is increased or decreased based on the metric indicative of cardiac performance.

FIG. 3 shows a plot 300 of pressure versus time for a heart pump system, according to certain implementations. The y-axis of plot 300 represents aortic pressure in mmHg, while the x-axis represents time as a percentage of a heartbeat length. In particular, plot 300 shows the effect of pinging on aortic pressure. $t_1$ represents a time of a first heartbeat and $t_2$ represents a time of a second heartbeat after the first heartbeat. Time periods $t_1$ and $t_2$ occur while the heart pump system is placed at least partially within the patient's heart. Point 310 represents systolic peak pressure during the first heartbeat and point 320 represents systolic peak pressure during the second heartbeat. Point 312 represents the dicrotic notch during the first heartbeat and point 322 represents the dicrotic notch during the second heartbeat. Diastolic time periods $t_3$ and $t_4$ represent the diastolic period of the first and second heartbeats, respectively. During time period $t_1$, the pump operates at a first pump speed. During time period $t_4$ the pump operates at a second pump speed greater than the first pump speed.

At higher pump speeds, the measured aortic pressure and total flow are higher compared to lower pump speeds. Accordingly, during diastolic period $t_4$ when the pump operates at the second pump speed greater than the first pump speed, the aortic pressure is higher than the aortic pressure during diastolic period $t_3$ when the pump operates at the first pump speed. The difference in aortic pressure between diastolic periods $t_3$ and $t_4$ is shown by shaded area 324. This difference correlates to an increase in flow and CO during the same time period $t_4$.

Figure 4:
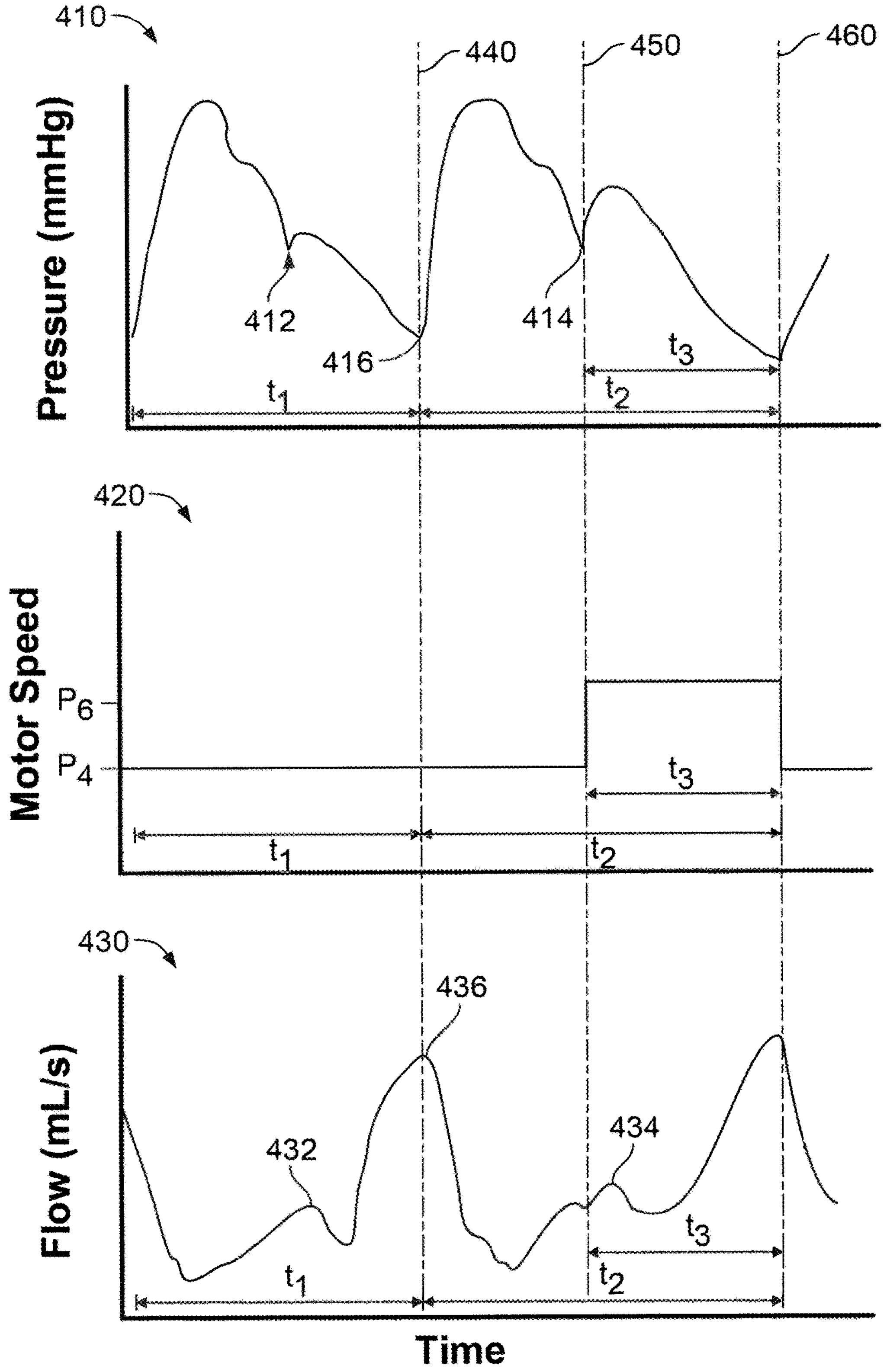
FIG. 4 shows plots of pressure, motor speed, and flow versus time according to certain implementations.

FIG. 4 shows plots of pressure, motor speed, and flow versus time. The y-axis of pressure plot 410 represents aortic pressure in mmHg, the y-axis of motor speed plot 420 represents motor speed by P-level, and the y-axis of flow plot 530 represents flow in mL/s. The x-axis of plots 410, 420, 430 represents time as a percentage of a heartbeat length. For all three plots, $t_1$ represents a time of a first heartbeat and $t_2$ represents a time of a second heartbeat after the first heartbeat. Time periods $t_1$ and $t_2$ occur while the heart pump system is placed at least partially within the patient's heart. At time 440, the second heartbeat starts. At time 450, the diastolic period $t_3$ of the second heartbeats starts. At time 460, the second heartbeat ends.

Pressure plot 410 is similar to plot 300 described above. Point 410 represents the dicrotic notch of the first heartbeat, point 414 represents the dicrotic notch of the second heartbeat, and point 416 represents the start of the systolic upstroke of the second heartbeat. At time 450, corresponding to point 410 (the dicrotic notch of the first heartbeat) of plot 410, the pump speed is increased as shown in motor speed plot 420. During time period $t_1$, the pump operates at pump speed P-4. During diastolic period $t_3$, the pump operates at pump speed P-6. There may be a time delay between when a controller sends a signal to the pump to alter pump speed and when the pump speed is increased. As can be seen in pressure plot 410 and flow plot 430, during time period $t_3$, when the pump speed is increased to P-6, the flow and the pressure both increase.

Figure 5:
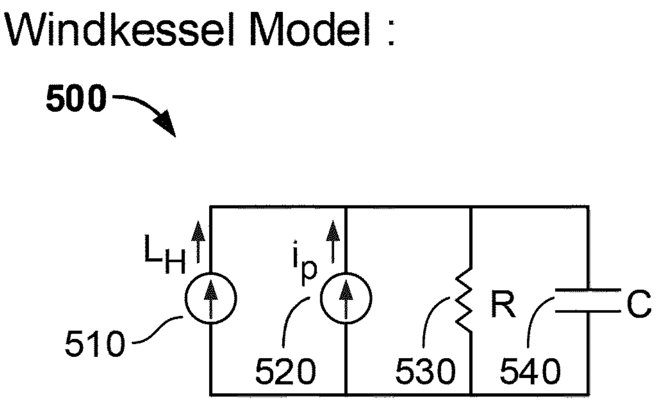
FIG. 5 shows a Windkessel model according to certain implementations.

FIG. 5 shows a Windkessel model 500. Windkessel model 500 includes current source 510, current source 520, resistance 530, and compliance 540. The governing equation for this model is:

$$C\frac{dP}{dt} + \frac{P}{R} = i_h + i_p \tag{2}$$

where C is compliance, P is pressure, R is systemic resistance, $i_h$ is flow from native heart operation and $i_p$ is flow from the pump. During diastole, however, the aortic valve is closed, so the only flow through the left ventricle is from the pump positioned across the valve. By discounting the heart current source and assuming pump flow is constant, the model can thus be simplified as follows:

$$P = P_0 e^{-\frac{t}{RC}} + i_p R \tag{4}$$

where $P_0$ is the initial aortic pressure during diastole. Resistance and compliance may be then determined via the following two equations, where P1 and P2 are pressure waveforms measured at different pump speeds:

$$P_1 = P_{01} e^{-\frac{t}{RC}} + i_{p1} R \tag{5}$$

$$P_2 = P_{02} e^{-\frac{t}{RC}} + i_{p2} R \tag{6}$$

At low pump speeds, $i_{p1}R$ may be approximated as zero, resulting in a simple exponential for Equation (5). After determining R using Equation (6) and this simplification, the $i_{p1}R$ term may be added back to Equation (5) to then accurately determine C.

Vascular state can be thus determined through analysis of the aortic pressure waveform measured by the heart pump system by measuring the difference in aortic pressure induced by heart pump speed changes with the underlying assumption that the vascular state remains stable over this interval. Systemic vascular resistance is determined by using the above equations at two different Impella operating points and the difference in estimated Impella flow rate. Cardiac performance can then be determined by using these vascular state values in the above general equation with the measured aortic pressure to calculate flow from the heart. The pulsatile ejection component of the flow rate waveform is numerically integrated over the ejection phase of the heartbeat cycle to estimate stroke volume or CO.

Figure 6:
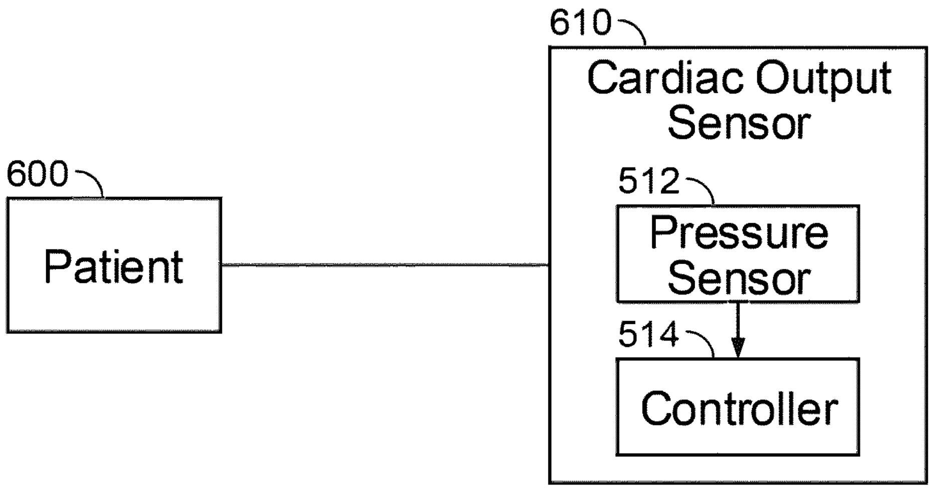
FIG. 6 shows a CO sensor coupled to a patient according to certain implementations.

FIG. 6 shows a CO sensor 610 coupled to a patient 600, with the CO sensor configured to determine native cardiac output. CO sensor 610 may comprise a variety of hardware elements configured to perform the methods described herein. In some implementations, the CO sensor includes an intravascular blood pump (e.g., pump 202 of FIG. 1) and a controller for operating the pump, receiving inputs indicative of pump operating conditions and intravascular pressure, and determining native cardiac. The intravascular blood pump may be configured to be placed at least partially within a patient's heart. In some implementations, the intravascular blood pump includes a cannula, a rotor configured to be rotated within a blood vessel and pump blood through the cannula, and a drive mechanism configured to impart power to turn the rotor. In some implementations, the cannula may be configured to extend across an aortic valve such that a distal end of the cannula is within a left ventricle and a proximal end of the cannula is within the aorta. For example, the heart pump system may be considered "in position" when the cannula is placed across the aortic valve such that a blood inlet to the pump is within the left ventricle and an outlet from the pump is within the aorta. The drive mechanism may include an onboard motor, a drive cable, a drive shaft, or any other suitable element or combination thereof.

In some implementations, CO sensor 610 includes an elongate catheter body coupled to a cannula. The elongate catheter may include a drive cable, electrical wiring connecting the blood pump to a control system, any suitable element, or any combination thereof. In some implementations, the blood pump includes a pump housing and a motor housing coupled to the cannula at a distal end of the motor housing. The rotor may be rotated within the pump housing to induce a flow of blood into the cannula.

CO sensor 610 includes a pressure sensor configured to detect pressure within the blood vessel arising at least in part from the pumping of blood within the vessel. For example, the pressure sensor may be an optical pressure sensor that is part of a blood pump, or a differential pressure sensor may be used. One side or surface of the differential pressure sensor may be exposed to the aortic pressure, a second side or surface of the differential pressure sensor may be exposed to the ventricular pressure, and the differential pressure sensor may measure the difference between the aortic and ventricular pressures. As another example, pressure sensor 612 may comprise a pressure measurement lumen configured to measure aortic pressure.

CO sensor 610 includes controller 614. Controller 614 is coupled to pressure sensor 612. Controller 614 may couple directly or indirectly to pressure sensor 612. For example, controller 614 may be connected to pressure sensor 612 via electrical wiring, a wireless signal, or any other suitable means. Controller 614 is configured to detect signals from the pressure sensor indicative of blood pressure. All or part of controller 614 may be in a controller unit separate/remote from an intravascular blood pump. In some implementations, the control system is internal to an intravascular blood pump.

In some implementations, controller 614 is configured to calculate CO based on a non-linear model that correlates CO to vascular resistance and compliance. For example, the nonlinear model may be a Windkessel model as described above in relation to FIG. 5.

Figure 7:
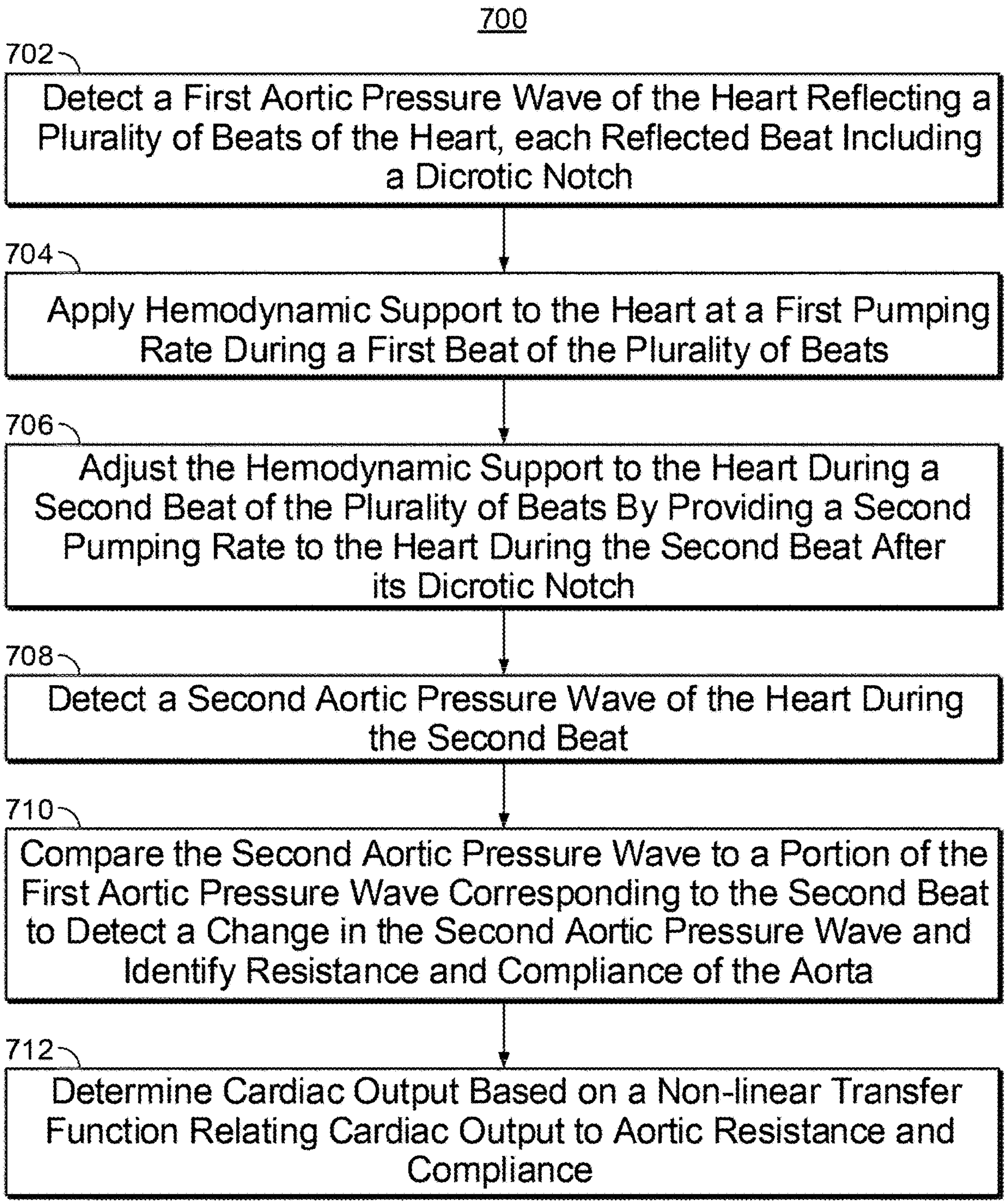
FIG. 7 illustrates a process for determining CO according to certain implementations.

FIG. 7 illustrates a process 700 for determining CO. The process 700 can be performed using the heart pump system 100 of FIG. 1 or any other suitable pump. In some implementations, the pump is an intravascular blood pump device placed within the patient's heart via percutaneous insertion. The pump may be introduced to the patient because the patient is in cardiogenic shock or otherwise experiencing a decline in health. The pump may be positioned across the aortic valve such that a blood inlet (e.g., blood inlet 172 of FIG. 1) to the pump is within the left ventricle and an outlet (e.g., outlet openings 170 of FIG. 1) from the pump is within the aorta. The pump contributes to native heart operation such that:

$$CO = i_h + i_p \quad (1)$$

where CO is total cardiac output, $i_h$ is native cardiac output, and $i_p$ is flow contributed by the pump At step 702, a first aortic pressure wave is detected. The first aortic pressure wave reflects a plurality of beats of the heart, each reflected beat including a dicrotic notch. The pressure waveform may be measured via a pressure sensor. In some implementations, the pressure sensor may be on board the pump. In some implementations, the pressure sensor may be located externally from the pump. The pressure sensor may communicate with a controller configured to control operation of the pump.

At step 704, hemodynamic support is applied to the heart at a first pumping rate during a first beat of the plurality of beats. For example, the first pumping rate may be a first rotor speed, such as a P-level described above. At step 706, the hemodynamic support to the heart is adjusted during a second beat of the plurality of beats by providing a second pumping rate to the heart during the second beat after its dicrotic notch. The first pumping rate is different from the second pumping rate.

At step 708, a second aortic pressure wave of the heart is detected during the second beat. At step 710, the second aortic pressure wave is compared to a portion of the first aortic pressure wave corresponding to the second beat to detect a change in the second aortic pressure wave. The change between the first and second aortic pressure waves may be used to identify resistance and compliance of the systemic vasculature.

At step 712, CO is determined based on a non-linear transfer function relating CO to systemic resistance and compliance. The transfer function may further relate to the aortic pressure waveform. In some implementations, the non-linear transfer function includes a Windkessel model, such as that described above in relation to FIG. 5.

Figure 8:
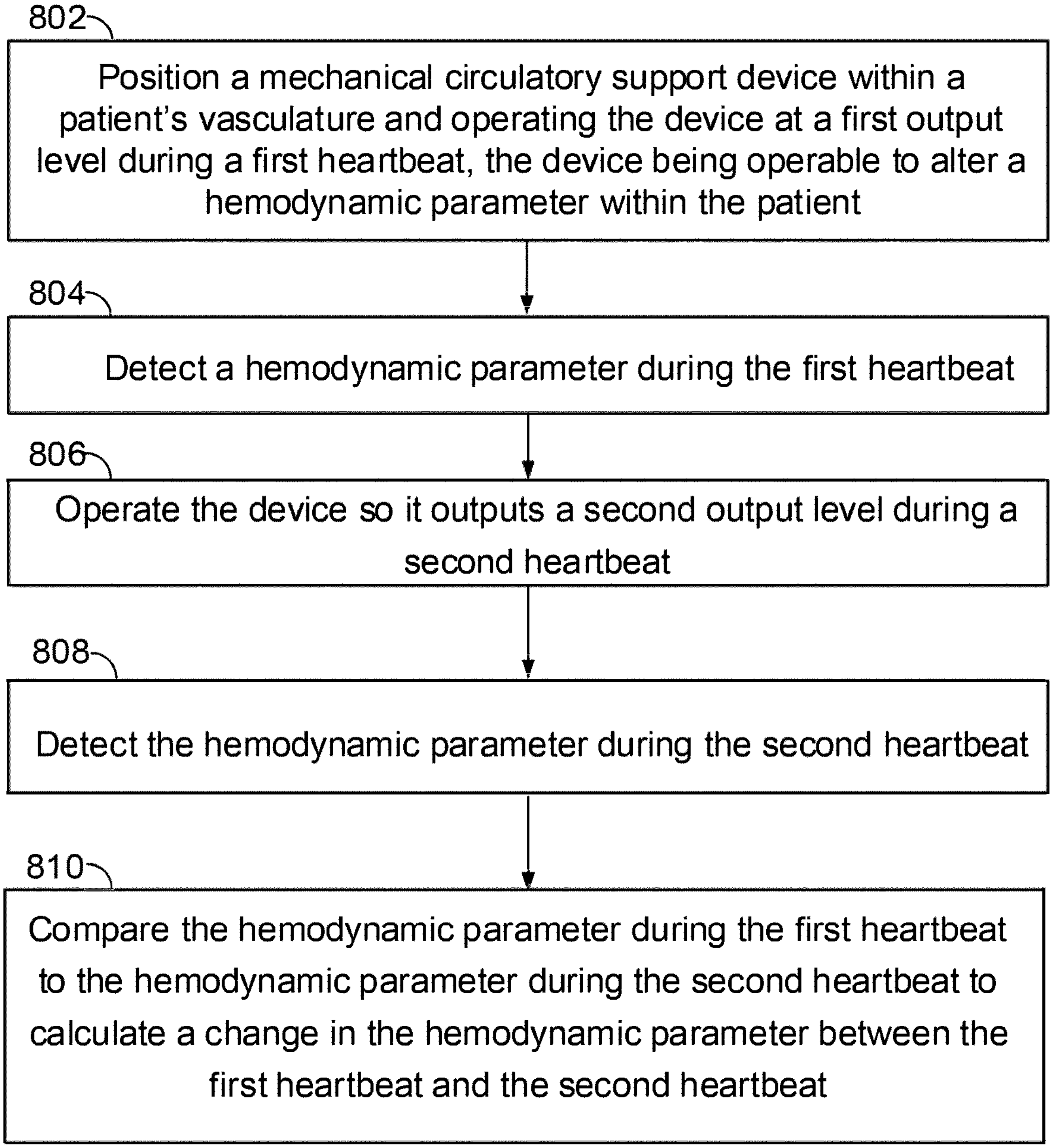
FIG. 8 illustrates a process for determining a change in hemodynamic parameter between two heartbeats according to certain implementations.

FIG. 8 illustrates a process 800 for determining a change in a hemodynamic parameter between two heartbeats. At step 802, a mechanical circulatory support device is positioned within a patient's vasculature. In some implementations, the device is an intravascular blood pump device placed within the patient's heart via percutaneous insertion. The device may be introduced to the patient because the patient is in cardiogenic shock or otherwise experiencing a decline in vascular health. The device may be a left heart device or a right heart device. In some implementations, the device is positioned across the aortic valve such that a blood inlet (e.g., blood inlet 172 of FIG. 1) to the device is within the left ventricle and an outlet (e.g., outlet openings 170 of FIG. 1) from the device is within the aorta.

The device is operable to alter a hemodynamic parameter within the patient. For example, the device's operation may affect the patient's aortic pressure by pumping blood from the left ventricle and into the aorta. The device is operated at a first output level and while the heart is beating. The first output level corresponds to a first rate of blood flow contributed by the mechanical circulatory support device to the patient's native blood flow during device operation at the first output level. For example, the first output level may be associated with a first motor speed, such as the P-levels described above.

The device operates at the first output level for a period of time which includes the period of a first heartbeat, and the hemodynamic parameter of the patient is monitored during the operation of the device, such that the results of that monitoring are determined as a function of time within each heartbeat and stored in the device memory (or other data storage device). As described above, a hemodynamic parameter is any parameter relating to the flow of blood within the organs and tissues of the body. At step 804, a hemodynamic parameter is detected during the first heartbeat and coincides temporally with the first heartbeat. The device output level and hemodynamic parameter measurements during that heartbeat (or any other time during the first output level) coincide with the events of the heartbeat cycle (e.g., systole, diastole, dicrotic notch). As a result, the hemodynamic parameter and device output levels can be correlated with the events of the cardiac cycle at various points in time during the heartbeat. For example, it can readily be detected that the pump operating at a first output level will have a first measured hemodynamic parameter (e.g., aortic pressure) at or after the dicrotic notch of a first heartbeat. In some implementations, the hemodynamic parameter is aortic pressure, and the mechanical circulatory support device includes a pressure sensor configured to detect aortic pressure. In some adaptations, the pressure sensor is included on a cannula extending partially within the patient's left ventricle.

At step 806, the device is operated so that it outputs a second output level during a second period of time, including during one or more periods of time within a second heartbeat. The second output level (delivered during the second heartbeat) may be greater or less than the first output level (delivered during the first heartbeat). For example, the second output level may be associated with a second motor speed or P-level greater or less than the first motor speed and that output level can be delivered during the second heartbeat at the same phase point as when the first output level is delivered (e.g., at or after the dicrotic notch).

At step 808, the hemodynamic parameter is detected during the second heartbeat (during the period of that second output level) at or near the same point in the cardiac phase of the second heartbeat as in the first heartbeat. The hemodynamic parameter may be measured during the entirety of the first or second heartbeat or for a portion of the respective beat. For example, the hemodynamic parameter may be measured during systole or diastole of the second heartbeat, or at the dicrotic notch.

At step 810, the hemodynamic parameter measured during the first heartbeat is compared to the hemodynamic parameter measured during the second heartbeat. These two measurements are taken at approximately the same point in the cardiac cycle, albeit during two different beats. The difference in hemodynamic measurement arises because of the change in pump speed between the first heartbeat and the second heartbeat. For example, if the hemodynamic parameter is aortic pressure, increasing the output level will increase measured aortic pressure and decreasing the output level will decrease measured aortic pressure. This change in aortic pressure from the first output level to the second output level correlates with the mechanical circulatory support device's contribution to the change in total cardiac output.

Figure 9:
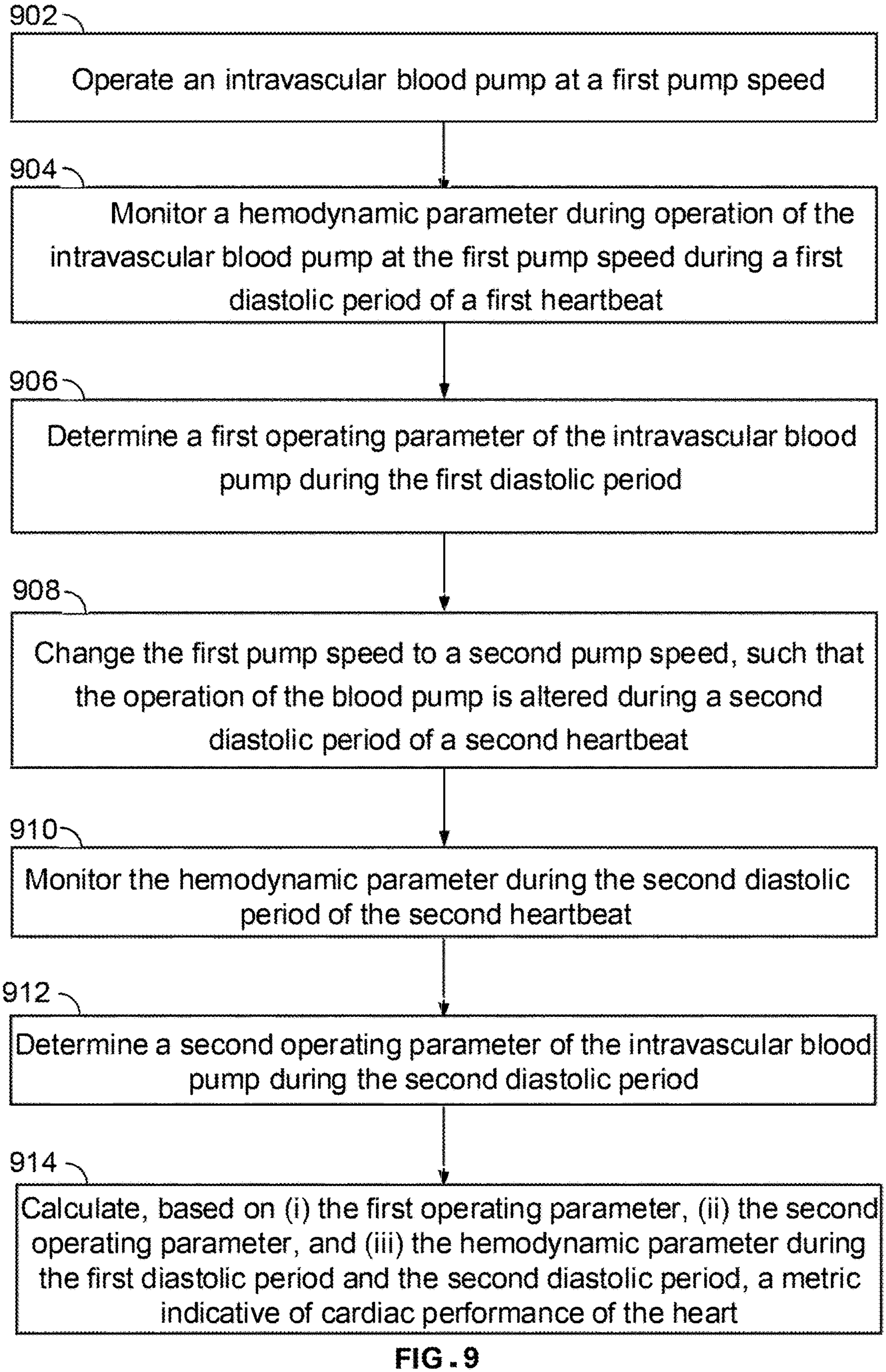
FIG. 9 illustrates a process for determining CO according to certain implementations.

FIG. 9 illustrates a process 900 for determining cardiac output by a heartbeat "pinging" process. The process 900 can be performed using the heart pump system 100 of FIG. 1 or any other suitable pump. The pump is placed within the patient's heart via percutaneous insertion. The patient may be in cardiogenic shock or otherwise experiencing a decline in vascular health. The pump may be a left heart device or a right heart device. The pump is positioned across the aortic valve such that a blood inlet (e.g., blood inlet 172 of FIG. 1) to the pump is within the left ventricle and an outlet (e.g., outlet openings 170 of FIG. 1) from the pump is within the aorta. The pump contributes to native heart operation such that:

$$CO = i_h + i_p \quad (1)$$

where CO is total cardiac output, $i_h$ is native cardiac output, and $i_p$ is flow contributed by the pump.

At step 902, the pump is operated at a first pump speed during a first period of time, including a period of a first heartbeat. At step 904, a hemodynamic parameter is monitored during operation of the heart pump at the first pump speed during a first diastolic period of the first heartbeat. The hemodynamic parameter relates to the flow of blood within the body. The pump speed is the speed of operation of the pump and corresponds to the amount of blood flow provided by the pump's operation. In some implementations, the pump speed corresponds to the rotational speed of the pump's rotor. For example, the pump speed may be at or above 10,000 RPM, 20,000 RPM, 30,000 RPM, 40,000 RPM, 50,000 RPM, 60,000 RPM, 70,000 RPM, 80,000 RPM, 90,000 RPM, 100,000 RPM, or any suitable speed. A pump speed may correspond to a power level, or P-level, as described above in relation to FIG. 1. For example, the pump speed may be P-1, P-2, P-3, P-4, P-5, P-6, P-7, P-8, P-9, or any other suitable value. In some implementations, the pump speed corresponds to the rate at which a chamber of the pump fills and releases blood. By monitoring a hemodynamic parameter, the systems and methods described herein may identify changes in that hemodynamic parameter over time, including during the phases of first and second heartbeats. Such comparisons may be used to quantify heart performance (e.g., through CO), as discussed more fully herein.

At step 906, a first operating parameter is determined for the intravascular blood pump during the diastolic period. For example, the operating parameter may be current supplied to the pump, a rate of blood flow provided by the pump, or placement of the pump within the patient's vasculature. Specifically, determining the first operating parameter may comprise determining a first rate of blood flow provided by the blood pump during the diastolic period. This first operating parameter and the measured hemodynamic parameter may be identified at a particular point in the heartbeat cycle of the first heartbeat. Flow from the pump is estimated based on the motor current supplied to a motor in the blood pump to maintain the pump speed.

For a given intravascular blood pump system, the flow output $i_p$ can be determined by the speed of the pump (round per minute or RPM) and the motor current supplied to the pump to maintain operation at that pump speed. This mathematical calculation from pump speed and motor current to the flow can be implemented by setting up a look-up table where the pump speed and motor current are the indices to the table and the flow values in the table is pre-populated through bench testing. Another way is to pre-determine flow for a sub-set of possible combinations of pump speed and motor current. For example, if flow $i_1$ is representative of flow at a pump speed of 40,000 RPM and a motor current of 500 mA and flow $i_2$ is representative of flow at a pump speed of 40,000 RPM and a motor current of 510 mA, then the flow $i_3$ at a pump speed of 40,000 RPM and a motor current of 505 mA may be calculated by taking the average of $i_1$ and $i_2$.

At step 908, the first pump speed is changed to a second pump speed, such that the operation of the heart pump delivers a second output level during a second diastolic period of a second heartbeat. The second pump speed may be greater or less than the first pump speed. In some implementations, the pump speed increase is timed such that the increased pump speed occurs during a predicted period of the heartbeat. For example, the beginning of the speed increase may be synchronized with the start of diastole to account for any delay between sending an instruction to the pump to change the speed and when that change in speed physically occurs. The end of the speed increase may be synchronized with the start of diastole, the end of diastole, the start of systole, the end of systole, peak systolic pressure, or any other suitable time. In some implementations, the system is configured so the pump speed is increased or decreased for a set period of time. For example, the speed change may last for about 0.05 seconds, 0.1 seconds, 0.2 seconds, 0.3 seconds or any other suitable length of time. The second heartbeat is different than the first heartbeat.

At step 910, the hemodynamic parameter is monitored during the second diastolic period of the second heartbeat, e.g., at the diachrotic notch. At step 912, a second operating parameter of the intravascular blood pump during the second diastolic period is determined. Determining the second operating parameter may comprise determining a second rate of blood flow (or a second level of a motor operating parameter) provided by the blood pump during the second diastolic period.

At step 914, a metric indicative of cardiac performance of the heart is calculated. The metric is based on (i) the first operating parameter, (ii) the second operating parameter, and (iii) the hemodynamic parameter during the first diastolic period and the second diastolic period (e.g., at the diachrotic notch during both periods). The metrics may be used in a transfer function or set of equations such as those described above in relation to the Windkessel model. In some implementations, a mathematical representation of the hemodynamic parameter is determined for the first and second diastolic periods. For example, the mathematical representation may be a summation of sinusoids.

The metrics are used to construct a waveform which can be used to determine cardiac output. Computing cardiac performance may include deconstructing a first waveform representative of the hemodynamic parameter for the first diastolic period to determine a first set of sinusoids, and deconstructing a second waveform representative of the hemodynamic parameter for the second diastolic period to determine a second set of sinusoids. These deconstructions may include applying a Fourier transform to the first waveform, the second waveform, or both. A set of sinusoids may include one or more sinusoids summed together.

While the pump is operating within the patient's vasculature, the blood flow within the aorta is equal to the pump contribution ($i_p$) plus the native heart contribution ($i_h$). The first set of sinusoids and the second set of sinusoids may be compared to determine the contribution of the patient's heart ($i_h$) to blood flow within the aorta. For example, aortic pressure may be the hemodynamic parameter, and the aortic pressure may be expressed as a summation of sinusoids resulting from the Fourier transform, as $$P = \sum_{n=1}^{N} A_n \sin(f_n t + \theta_n)$$

where P is the aortic pressure, $f_n$ is a frequency associated with an operating parameter, and $A_n$ and $\theta_n$ are coefficients for the operating parameter. The difference in the sets of sinusoids between operating parameters may be used to calculate the difference in flow between the operating parameters because the change in pressure between operating parameters will be proportional to the change in flow. In some implementations, the Fourier transform may be calculated for each pump speed in a range of pump speeds. In some implementations, patient response to the "pinged" pump speed may be minimal due to the limits on speed changes in a short period of time (i.e., the time it takes to ramp up a pump to an increased speed or slow down the pump to a decreased speed).

Decomposing the hemodynamic parameter over time into its constituent frequencies allows the hemodynamic parameter to be determined using a mathematical equation or set of equations. In some implementation, the mathematical representation is an exponential equation based on the comparison of sinusoids. After the hemodynamic parameter waveform has been characterized by a mathematical equation, heart parameters such as vascular resistance and compliance may be determined from the equation. For example, if the hemodynamic parameter wave form is characterized as a series of exponential functions in the form of $$P = Ae^{\frac{-t}{B}} + D$$

(where B is equal to R*C and D is equal to $i_p$*C, P is pressure, R is systemic resistance, and C is systemic compliance), then systemic resistance and compliance values may be calculated by solving a system of equations with these coefficients at two points in time (i.e., with two known pressure measurements).

In some implementations, a model heartbeat representative of the patient's heart function may be simulated based on the comparison of sinusoids and used to determine cardiac output, determine when to apply mechanical circulatory support, and what levels. For example, the blood pump may be operated at a range of pump speeds (e.g., P-1, P-2, P-3, P-4, etc.) where each pump speed corresponds to a rate of rotation of a rotor within the pump and analogous frequency (e.g., 100 Hz, 200 Hz, 300 Hz, 400 Hz, 500 Hz, 1000 Hz, 2000 Hz, 3000 Hz, etc.). Changing the pump speed (or frequency) will change the value of the hemodynamic parameter because it will change the flow of blood in the vasculature provided by the pump's operation. By gradually stepping through multiple pump speeds (or operating parameters, such as blood flow provided by the pump) to identify corresponding changes to one or more hemodynamic parameters, forming a hemodynamic waveform, and deconstructing the hemodynamic waveform resulting from each pump speed, a relationship between pressure and flow during diastole is established. The patient's overall heart function can then be mapped as a mathematical representation (as a function of the measured hemodynamic parameters) that can be used to simulate future heart function and inform delivery and control of mechanical circulatory support to the patient. For example, the measured aortic pressure waveform of any recorded heartbeat may be constructed using the methods described below—allowing the CO to be calculated for that heartbeat.

As described above, in some implementations, a brief change in pump speed can be applied to the pump within one heartbeat. This change in pump speed may be considered as an impulse stimulus. The aortic pressure recorded for this heartbeat may be compared to the aortic pressure of a heartbeat without this brief speed change or impulse stimulus. The difference of the two (the aortic pressure of the altered heartbeat and the aortic pressure of a "normal" heartbeat) may be considered the impulse response of the aortic pressure:

$$\Delta p(t) = p_1(t) - p_2(t)$$

where $P_1(t)$ is the pressure waveform measured with the impulse stimulus, $P_2(t)$ is the pressure waveform without the impulse stimulus, and $\Delta P(t)$ is the impulse response of the aortic pressure.

If this impulse stimulus is only applied during diastole, then the difference in the total cardiac flow for the two heartbeats can be represented as:

$$\Delta i(t) = i_1(t) - i_2(t)$$

where $i_1(t)$ and $i_2(t)$ are the pump flow for the heartbeat with the impulse stimulus and the heartbeat without the impulse stimulus, respectively, and $\Delta i(t)$ is the impulse response of the cardiac flow.

Then the aortic pressure vs. pump flow relationship can be estimated in frequency domain as:

$$H(f) = \frac{\Delta P(f)}{\Delta I(f)}$$

where $\Delta P(f)$ is frequency domain representation (e.g., Fast Fourier Transform or FFT) of $\Delta p(t)$, $\Delta I(f)$ is the frequency domain representation of $\Delta i(t)$, and $H(f)$ is the frequency domain transfer function for the aortic pressure versus pump flow relationship.

Once this relationship $H(f)$ is established as outlined above, the total cardiac flow for any heartbeat with aortic pressure measured as $p(t)$ can be calculated as:

$$\text{total\_i}(t) = IFFT\left(\frac{P(f)}{H(f)}\right)$$

where $P(f)$ is the frequency domain representation of $p(t)$ and IFFT is the Inverse Fast Fourier Transform.

Figure 10:
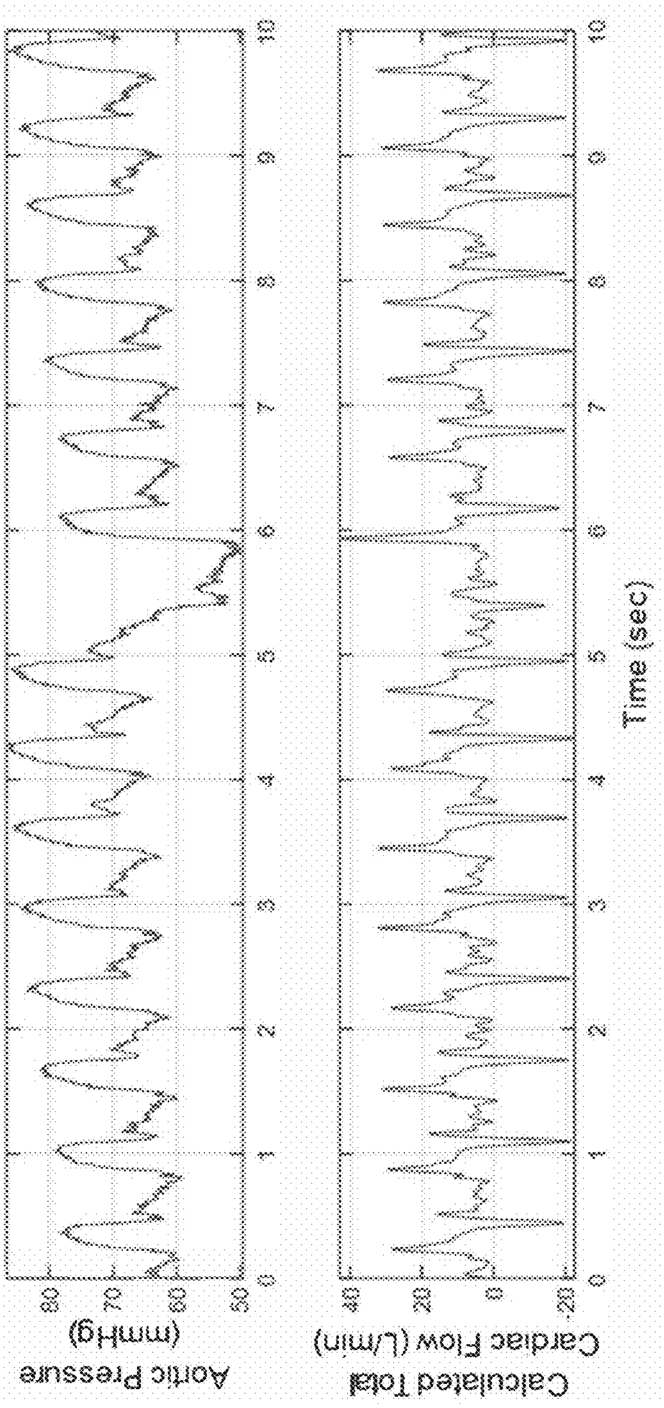
FIG. 10 shows two exemplary graphs showing aortic pressure and cardiac flow for the same ten-second period according to certain implementations.

FIG. 10 shows two plots, one of aortic pressure and one of cardiac flow for the same ten-second period. The y-axis of the upper plot represents aortic pressure in mmHg, while the x-axis represents time in seconds. The y-axis of the lower plot represents calculated total cardiac flow in liters per minute, while the x-axis represents time in seconds. In this example, systemic vascular resistance R and compliance C are known. For example, R and C may be calculated using aortic pressure measurements taken during the depicted ten second time period in combination with pump data as described above. The total cardiac flow $i_h+i_p$ is calculated using R, C, and the aortic pressure waveform by applying Equation (2):

$$C\frac{dP}{dt} + \frac{P}{R} = i_h + i_p \tag{2}$$

CO can be calculated by taking the average of the total cardiac flow $i_h+i_p$ resulting from Equation (1) over a period of time (e.g., 5 seconds, 10 seconds, or 30 seconds). In the example in FIG. 7, the period of time is 10 seconds. The average R value for the time period is 0.6143 mmHg*sec/ml and the average C value is 1.5 mL/mmHg, resulting in a calculated CO of 6.9 L/min.

The foregoing is merely illustrative of the principles of the disclosure, and the apparatuses can be practiced by other than the described aspects, which are presented for purposes of illustration and not of limitation. It is to be understood that the apparatuses disclosed herein, while shown for use in percutaneous insertion of heart pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

The systems and methods described may be implemented locally on a heart pump system or a controller of a heart pump system, such as the AIC. The heart pump system may comprise a data processing apparatus. The systems and methods described herein may be implemented remotely on a separate data processing apparatus. The separate data processing apparatus may be connected directly or indirectly to the heart pump system through cloud applications. The heart pump system may communicate with the separate data processing apparatus in real-time (or near real-time).

In general, aspects of the subject matter and the functional operations described in this specification can be implemented in digital electronic circuitry, or in computer software, firmware, or hardware, including the structures disclosed in this specification and their structural equivalents, or in combinations of one or more of them. Aspects of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program may correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method for determining cardiac output of a heart of a patient using a processor controlled intravascular device, comprising the steps of:

detecting a first aortic pressure wave of the heart reflecting a plurality of beats of the heart, each reflected beat including a dicrotic notch;

applying hemodynamic support to the heart at a first pumping rate during a first beat of the plurality of beats;

adjusting the hemodynamic support to the heart during a second beat of the plurality of beats by providing a second pumping rate to the heart during the second beat after a dicrotic notch of the second beat;

detecting a second aortic pressure wave of the heart during the second beat;

comparing, by the processor, the second aortic pressure wave to a portion of the first aortic pressure wave corresponding to the second beat to detect a change in the second aortic pressure wave and identify resistance and compliance of vasculature of the patient; and determining native cardiac output of the heart based on a non-linear transfer function, the non-linear transfer function relating cardiac output to vascular resistance and compliance.

2. The method of claim 1, wherein the non-linear transfer function includes a Windkessel model.

3. The method of claim 2, wherein the hemodynamic support is provided by an intracardiac blood pump that has a cannula configured to be positioned across aortic valve of the patient.

4. The method of claim 3, further comprising adjusting the hemodynamic support based on at least one of: the determined native cardiac output, the resistance, or the compliance.

5. The method of claim 1, further comprising adjusting the hemodynamic support to the heart to the first pumping rate following the second beat after the dicrotic notch of the second beat.

6. The method of claim 1, wherein detecting the first aortic pressure wave includes measuring the first aortic pressure wave via a pressure sensor.

7. The method of claim 6, wherein the pressure sensor is included in an intracardiac blood pump that has a cannula configured to be positioned across aortic valve of the patient.

8. The method of claim 1, wherein the first pumping rate and the second pumping rate are different.

* * * * *